(12) United States Patent
  Meuleman

(10) Patent No.: US 11,195,596 B2
(45) Date of Patent: Dec. 7, 2021

(54) ANALYZING CHARACTERISTICS OF GENOMIC REGIONS OF A GENOME

(71) Applicant: Massachusetts Institute of Technology, Cambridge, MA (US)

(72) Inventor: Wouter Meuleman, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 213 days.

(21) Appl. No.: 15/547,240

(22) PCT Filed: Jan. 29, 2016

(86) PCT No.: PCT/US2016/015629
§ 371 (c)(1),
(2) Date: Jul. 28, 2017

(87) PCT Pub. No.: WO2016/123472
PCT Pub. Date: Aug. 4, 2016

(65) Prior Publication Data
US 2018/0025110 A1    Jan. 25, 2018

Related U.S. Application Data

(60) Provisional application No. 62/109,111, filed on Jan. 29, 2015.

(51) Int. Cl.
*G01N 33/48* (2006.01)
*G01N 33/50* (2006.01)
(Continued)

(52) U.S. Cl.
CPC ............. *G16B 30/00* (2019.02); *G16B 20/00* (2019.02); *G16B 20/20* (2019.02)

(58) Field of Classification Search
CPC ................................ G16B 30/00; G16B 20/00
See application file for complete search history.

(56) References Cited

U.S. PATENT DOCUMENTS

2013/0296183 A1    11/2013    Eggan et al.

OTHER PUBLICATIONS

Roudier et al. Integrative epigenomic mapping defines four main chromatin states in *Arabidopsis*. EMBO J. vol. 30, pp. 1928-1938. (Year: 2011).*

(Continued)

*Primary Examiner* — Karlheinz R. Skowronek
(74) *Attorney, Agent, or Firm* — Wolf, Greenfield & Sacks, P.C.

(57) ABSTRACT

Embodiments of techniques for analyzing one or more genomic regions of a genome of an organism. Data about a genomic region may be analyzed to determine an information content of the genomic region, which may indicate an amount of information provided by the genomic region. The data about the genomic region may be or include data identifying a chromatin state for the genomic region. A chromatin state may be one of a set of chromatin states that each define a different set of one or more chromatin characteristics. Chromatin characteristics may be structural and/ or functional features of genomic regions. A chromatin state of a genomic region may be determined from, and describe, the genomic region such that when a genomic region has a set of one or more chromatin characteristics, a chromatin state associated with that combination of one or more chromatin characteristics is identified for the genomic region.

17 Claims, 15 Drawing Sheets

(51) Int. Cl.
  *G16B 30/00* (2019.01)
  *G16B 20/00* (2019.01)
  *G16B 20/20* (2019.01)

(56) References Cited

OTHER PUBLICATIONS

Bailey et al., Fitting a mixture model by expectation maximization to discover motifs in biopolymers. Proc Int Conf Intell Syst Mol Biol. 1994;2:28-36.

Ernst et al., ChromHMM: automating chromatin-state discovery and characterization. Nat Methods. Feb. 28, 2012;9(3):215-6. doi: 10.1038/nmeth.1906.

Ernst et al., Discovery and characterization of chromatin states for systematic annotation of the human genome. Nat Biotechnol. Aug. 2010;28(8):817-25. doi: 10.1038/nbt.1662. Epub Jul. 25, 2010.

Ernst et al., Mapping and analysis of chromatin state dynamics in nine human cell types. Nature. May 5, 2011;473(7345):43-9. doi: 10.1038/nature09906. Epub Mar. 23, 2011.

Halachev et al., EpiExplorer: live exploration and global analysis of large epigenomic datasets. Genome Biol. Oct. 3, 2012;13(10):R96. doi: 10.1186/gb-2012-13-10-r96.

Hoffman et al., Unsupervised pattern discovery in human chromatin structure through genomic segmentation. Nat Methods. Mar. 18, 2012;9(5):473-6. doi: 10.1038/nmeth.1937.

Mikkelsen et al., Genome-wide maps of chromatin state in pluripotent and lineage-committed cells. Nature. Aug. 2, 2007;448(7153):553-60. Epub Jul. 1, 2007.

Schneider, Consensus sequence Zen. Appl Bioinformatics. 2002;1(3):111-9.

Tanaka et al., Positional variations among heterogeneous nucleosome maps give dynamical information on chromatin. Chromosoma. Aug. 2010;119(4):391-404. doi: 10.1007/s00412-010-0264-y. Epub Mar. 12, 2010.

[Modencode Consortium], Identification of functional elements and regulatory circuits by *Drosophila* modENCODE. Science. Dec. 24, 2010;330(6012):1787-97. doi: 10.1126/science.1198374. Epub Dec. 22, 2010.

[Roadmap Epigenomics Consortium], Integrative analysis of 111 reference human epigenomes. Feb. 19, 2015;518(7539):317-30. doi: 10.1038/nature14248.

Davis et al., Entering the era of bacteria epigenomics with single molecule real time DNA sequencing. Curr Opin Microbiol. 2013;16(2):192-8.

Eads et al., MethyLight: a high-throughput assay to measure DNA methylation. Nucleic Acids Res. Apr. 15, 2000;28(8):E32, 8 pages.

Egelhofer et al., An assessment of histone-modification antibody quality. Nat Struct Mol Biol. Jan. 2011;18(1):91-3. doi: 10.1038/nsmb.1972. Epub Dec. 5, 2010.

Filion et al., Systematic protein location mapping reveals five principal chromatin types in *Drosophila* cells. Cell. Oct. 15, 2010;143(2):212-24. doi: 10.1016/j.cell.2010.09.009. Epub Sep. 30, 2010.

Gerstein et al., Integrative analysis of the Caenorhabditis elegans genome by the modENCODE project. Science. Dec. 24, 2010;330(6012):1775-87. doi: 10.1126/science.1196914. Epub Dec. 22, 2010.

Kharchenko et al., Comprehensive analysis of the chromatin landscape in *Drosophila*. Nature. Mar. 24, 2011;471(7339):480-5. doi: 10.1038/nature09725. Epub Dec. 22, 2010.

Laird, Principles and challenges of genome-wide DNA methylation analysis. Nat Rev Genetics. 2010;11:191-203.

Liu et al., Broad chromosomal domains of histone modification patterns in C. elegans. Genome Res. Feb. 2011;21(2):227-36. doi: 10.1101/gr.115519.110. Epub Dec. 22, 2010.

Riddle et al., Plasticity in patterns of histone modifications and chromosomal proteins in *Drosophila* heterochromatin. Genome Res. Feb. 2011;21(2):147-63. doi: 10.1101/gr.110098.110. Epub Dec. 22, 2010.

\* cited by examiner

ANALYZING CHARACTERISTICS OF GENOMIC REGIONS OF A GENOME

RELATED APPLICATIONS

This application claims priority as a national stage filing under 35 U.S.C. § 371 to PCT/international application Application No. PCT/US2016/015629, titled, "Analyzing Characteristics of Genomic Regions of a Genome" and filed on Jan. 29, 2016, which claims priority under 35 U.S.C. § 119(e) to U.S. Provisional Application Ser. No. 62/109,111, titled "Information-theoretic approach for analyzing chromatin state models" and filed on Jan. 29, 2015, the contents of both of which are herein incorporated by reference in their entirety.

GOVERNMENT SUPPORT

This invention was made with Government support under Grant No. R01 HG004037 awarded by the National Institutes of Health (NIH). The Government has certain rights in the invention.

FIELD

Embodiments relate to techniques for analyzing characteristics associated with genomic regions, including epigenomic characteristics associated with genomic regions of a genome of an organism. The techniques may be used to identify, such as from all of the genomic regions of a genome, genomic regions of interest for research or other purposes.

BACKGROUND

Epigenomic data provide information about the dynamic role of chromatin states in gene regulation. Mechanistic understanding of the determinants for chromatin states or how chromatin state segmentations vary under different conditions remains lacking.

SUMMARY

There is a need to develop methods or approaches for analyzing chromatin state models, which, for example, can be used to identify putative targets to control cell-specific functions, and/or provide a novel approach to therapy for a disease or disorder, e.g., cancer, and/or for diagnostic purposes.

In one embodiment, there is provided a method of analyzing one or more genomic regions for cells of one or more organisms having one or more genomes. The method comprises operating at least one processor to carry out an act of, for each genomic region of at least one genomic region, of a plurality of genomic regions of a genome for an organism, determining an information content of the genomic region. Determining the information content of the genomic region comprises receiving digital data identifying, for one or more cells of the organism having the genome, one or more chromatin states associated with the genomic region in the one or more cells, each of the chromatin states associated with the genomic region being a chromatin state from a set of two or more chromatin states, wherein each chromatin state of the set is associated with a different set of one or more chromatin characteristics, and determining the information content of the genomic region based at least in part on the digital data identifying the chromatin state associated with the genomic region in the one or more cells. The method further comprises operating at least one processor to carry out an act of storing the information content for each genomic region of the at least one genomic region in at least one data store.

In another embodiment, there is provided a method of analyzing one or more genomic regions for cells of one or more organisms having one or more genomes. The method comprises, for each genomic region of at least one genomic region, of a plurality of genomic regions of a genome for an organism, determining an information content of the genomic region. Determining the information content of the genomic region comprises receiving digital data identifying, for one or more cells of the organism having the genome, a chromatin state associated with the genomic region in the one or more cells, the chromatin state associated with the genomic region being a chromatin state from a set of two or more chromatin states, wherein each chromatin state of the set is associated with a different set of one or more chromatin characteristics, and determining the information content of the genomic region based at least in part on the digital data identifying the chromatin state associated with the genomic region in the one or more cells. The method further comprises storing the information content for each genomic region of the at least one genomic region in at least one data store.

In a further embodiment, there is provided a method of analyzing one or more genomic regions for cells of one or more organisms having one or more genomes. The method comprises operating at least one processor to carry out an act of for each genomic region of at least one genomic region, of a plurality of genomic regions of a genome for an organism, determining an information content of the genomic region. Determining the information content of the genomic region comprises receiving digital data identifying, for one or more cells of the organism having the genome, a chromatin state associated with the genomic region in the one or more cells, the chromatin state associated with the genomic region being a chromatin state from a set of two or more chromatin states, wherein each chromatin state of the set is associated with a different set of one or more chromatin characteristics, and determining the information content of the genomic region based at least in part on the digital data identifying the chromatin state associated with the genomic region in the one or more cells. The method further comprises operating the at least one processor to carry out an act of outputting, for display, at least one graphic for the at least one genomic region, wherein the at least one graphic indicates, for each genomic region of the at least one genomic region, the information content for the chromatin state for the genomic region.

In another embodiment, there is provided a method of analyzing one or more genomic regions for cells of one or more organisms having one or more genomes. The method comprises operating at least one processor to carry out an act of determining an information content for each of at least one genomic region of a plurality of genomic regions for both a first group of cells for one or more first organisms and a second group of cells for one or more second organisms, wherein the first group of cells comprises one or more types of cells and the second group of cells comprises the one or more types of cells. Determining an information content for a genomic region comprises determining the information content of the genomic region based at least in part on digital data identifying a chromatin state, from a set of chromatin states, associated with the genomic region in the one or more cells, wherein each chromatin state of the set is associated with a different set of one or more chromatin characteristics. The method further comprises operating the at least one processor to carry out acts of comparing the first information content for the first group of cells and the second information content for the second group of cells and determining whether the at least one genomic region is statistically significantly different between the first group of cells and the second group of cells based at least in part on a result of the comparing of the first information content for the first group of cells and the second information content for the second group of cells.

In a further embodiment, there is provided a method of analyzing one or more genomic regions for cells of one or more organisms having one or more genomes. The method comprises operating at least one processor to carry out acts of determining, for each of at least one genomic region of a plurality of genomic regions, an information content for each chromatin state associated with the genomic region in one or more cells, determining, for each genomic region of the at least one genomic region, a chromatin state for the genomic region that has the highest information content of chromatin states associated with the genomic region, and outputting, for each genomic region of the at least one genomic region, an identification of the genomic region and the determined chromatin state having the highest information content for the genomic region.

In another embodiment, there is provided a method of analyzing one or more genomic regions for cells of one or more organisms having one or more genomes. The method comprises operating at least one processor to carry out acts of receiving digital data identifying, for one or more cells of the organism having the genome, a chromatin state associated with the genomic region in the one or more cells, the chromatin state associated with genomic region being a chromatin state from a set of two or more chromatin states, wherein each chromatin state of the set is associated with a different set of one or more chromatin characteristics, determining, for each of at least one genomic region of a plurality of genomic regions, an information content for each chromatin state associated with the genomic region, evaluating the information content for each chromatin state associated with each genomic region of the at least one genomic region in the at least two groups of cells to identify patterns in occurrence of chromatin states and/or patterns of occurrence in chromatin states at genomic regions, and outputting an identification of each identified pattern.

In a further embodiment, in the method of any one or more of the foregoing embodiments, the digital data identifies chromatin states for at least two groups of cells for each genomic region, and determining the information content for each of the at least one genomic region based on digital data identifying the chromatin state comprises determining an information content for each chromatin state associated with the genomic region in the at least two groups of cells.

In another embodiment, in the method of any one or more of the foregoing embodiments, receiving the digital data identifying the chromatin state associated with the genomic region in the one or more cells comprises receiving digital data identifying chromatin states associated with the genomic region in at least two groups of cells, the at least two groups of cells comprising the one or more cells, and determining the information content based at least in part on the digital data identifying the chromatin state for the genomic region comprises comparing a relative occurrence of a chromatin state in the genomic region in the at least two groups of cells to an expected occurrence of the chromatin state in the at least two groups of cells.

In a further embodiment, in the method of any one or more of the foregoing embodiments, determining the information content for the genomic region comprises determining the information content for the genomic region from the information content for each of the chromatin states associated with the genomic region.

In another embodiment, in the method of any one or more of the foregoing embodiments, the digital data identifies chromatin states associated with each of at least two types of cells derived from organisms of one type having the genome and determining an information content for chromatin states associated with each of at least two types of cells for the organisms of one type.

In a further embodiment, in the method of any one or more of the foregoing embodiments, the digital data identifies one or more chromatin states in a single type of cell of the organism, and determining an information content for each of the at least one genomic region comprises determining an information content for the genomic region based on digital data identifying the chromatin state that appears at the genomic region in one or more cells of the single type of cell.

In another embodiment, in the method of any one or more of the foregoing embodiments, determining the information content based at least in part on the digital data identifying the one or more chromatin states for the genomic region comprises evaluating a probability of occurrence of the chromatin states at the genomic region.

In a further embodiment, in the method of any one or more of the foregoing embodiments, receiving the digital data identifying the chromatin state associated with the genomic region in the one or more cells comprises receiving digital data identifying chromatin states associated with the genomic region in at least two groups of cells, the at least two groups of cells comprising the one or more cells, and determining the information content based at least in part on the digital data identifying the chromatin state for the genomic region comprises comparing a relative occurrence of a chromatin state in the genomic region in the at least two groups of cells to an expected occurrence of the chromatin state in the at least two groups of cells.

In another embodiment, in the method of any one or more of the foregoing embodiments, the at least two groups of cells include cells of at least two types of cells of the organism having the genome, and the method further comprises receiving digital data identifying chromatin states associated with one or more other genomic regions in the at least two groups of cells, and determining the expected occurrence of the chromatin state based on occurrence of the chromatin state in the genomic region and the one or more other genomic regions in the at least two groups of cells.

In a further embodiment, in the method of any one or more of the foregoing embodiments, the at least two groups of cells include cells of at least two types of cells of the organism having the genome, and the method further comprises receiving digital data identifying chromatin states associated with one or more other genomic regions in the at least two groups of cells, and determining the expected occurrence of the chromatin state based on a number of times, for each genomic region of the genomic region and the one or more other genomic regions, that the chromatin state appears at the genomic region in cells of the at least two types of cells.

In another embodiment, in the method of any one or more of the foregoing embodiments, the at least two groups of cells include cells of at least two types of cells of the organism having the genome and the method further comprises receiving digital data identifying chromatin states associated with one or more other genomic regions in the at least two groups of cells, analyzing the digital data identifying the chromatin states associated with the genomic region and the one or more genomic regions in the at least two groups of cells to identify one or more relationships in occurrence of chromatin states in the genomic region and the one or more other genomic regions in the at least two groups of cells, and determining the expected occurrence of the chromatin state based at least in part on the one or more relationships in occurrence of chromatin states.

In a further embodiment, in the method of any one or more of the foregoing embodiments, the at least two groups of cells include cells of a single cell type. In another embodiment, in the method of any one or more of the foregoing embodiments, the method further comprises operating the at least one processor to carry out acts of determining one or more genomic regions of the at least one genomic region for which an information content of the chromatin state for the genomic region satisfies at least one criteria, and outputting an identification of the one or more genomic regions for which an information content satisfies the at least one criteria.

In another embodiment, in the method of any one or more of the foregoing embodiments, determining the one or more genomic regions of the at least one genomic region for which an information content of the chromatin states for the genomic region satisfies at least one criteria comprises determining genomic regions having an information content above a threshold.

In a further embodiment, in the method of any one or more of the foregoing embodiments, determining the one or more genomic regions of the at least one genomic region for which an information content of the chromatin states for the genomic region satisfies at least one criteria comprises comparing information content for multiple genomic regions of the at least one genomic region.

In another embodiment, in the method of any one or more of the foregoing embodiments, determining the information content for each genomic region of the at least one genomic region of the plurality of genomic regions of the genome for the organism comprises determining the information content for each genomic region of the at least one genomic region of the plurality of genomic regions of the genome for a first type of organism, and the method further comprises determining an information content for each genomic region of at least one second genomic region of a second plurality of genomic regions of a second genome for a second type of organism, and comparing the information content for each genomic region of the at least one genomic region and the at least one second genomic region.

In a further embodiment, in the method of any one or more of the foregoing embodiments, determining the information content for each genomic region of the at least one genomic region for the first type of organism comprises, for each genomic region, determining a first information content for each chromatin state associated with the genomic region, determining the information content for each genomic region of the at least one second genomic region for the second type of organism comprises, for each genomic region, determining a second information content for each chromatin state associated with the second genomic region, and comparing the information content for each genomic region of the at least one genomic region and the at least one second genomic region comprises, for each genomic region, determining a difference in information contents for one or more chromatin states in the genomic region between the first type of organism and the second type of organism and summing differences in information contents for the chromatin states for the genomic region.

In another embodiment, in the method of any one or more of the foregoing embodiments, the first type of organism is a male organism of a species and the second type of organism is a female organism of the species.

In a further embodiment, in the method of any one or more of the foregoing embodiments, the first type of organism is a first species and the second type of organism is a second species.

In another embodiment, in the method of any one or more of the foregoing embodiments, the first type of organism is an organism of a control group for a species and the second type of organism is an organism of the species having at least one characteristic that organisms of the at least one control group for the species do not have.

In a further embodiment, in the method of any one or more of the foregoing embodiments, the at least one characteristic is presence or absence of a medical condition, a higher likelihood of having a medical condition, exposure to a substance, or exposure to an environment.

In another embodiment, in the method of any one or more of the foregoing embodiments, the difference in information content is used as a marker to diagnose the medical condition in a subject.

In a further embodiment, in the method of any one or more of the foregoing embodiments, the difference in information content provides information to select a treatment or treatment regimen for the medical condition.

In another embodiment, in the method of any one or more of the foregoing embodiments, the method further comprises assaying a sample derived from the second type of organism to determine at least a portion of epigenome or chromatin states of at least a genomic region of the genome of the second type of organism.

In a further embodiment, in the method of any one or more of the foregoing embodiments, the sample comprises one or more cells, a tissue, or a bodily fluid.

In another embodiment, in the method of any one or more of the foregoing embodiments, the bodily fluid is one or more of plasma, blood, serum, or urine.

In a further embodiment, in the method of any one or more of the foregoing embodiments, the tissue is biopsy tissue.

In another embodiment, in the method of any one or more of the foregoing embodiments, the digital data identifies chromatin states for at least two groups of cells for each genomic region, determining an information content for each of the at least one genomic region based on digital data identifying the chromatin state comprises determining an information content for each chromatin state associated with the genomic region in the at least two groups of cells, and the method further comprises determining, for each genomic region of the at least one genomic region, a chromatin state for the genomic region that has the highest information content of chromatin states associated with the genomic region, and outputting, for each genomic region of the at least one genomic region, an identification of the genomic region and the determined chromatin state having the highest information content for the genomic region.

In a further embodiment, in the method of any one or more of the foregoing embodiments, the identification of the genomic region and the determined chromatin state having the highest information content for the genomic region provides a consensus region.

In another embodiment, in the method of any one or more of the foregoing embodiments, the digital data identifies chromatin states for at least two groups of cells for each genomic region, determining an information content for each of the at least one genomic region based on digital data identifying the chromatin state comprises determining an information content for each chromatin state associated with the genomic region in the at least two groups of cells, and the method further comprises determining, for each genomic region of the at least one genomic region, a chromatin state for the genomic region that has the lowest information content of chromatin states associated with the genomic region and outputting, for each genomic region of the at least one genomic region, an identification of the genomic region and the determined chromatin state having the lowest information content for the genomic region.

In a further embodiment, in the method of any one or more of the foregoing embodiments, the identification of the genomic region and the determined chromatin state having the lowest information content for the genomic region provides a nonsensus region.

In another embodiment, in the method of any one or more of the foregoing embodiments, the digital data identifies chromatin states for at least two groups of cells for each genomic region, determining an information content for each of the at least one genomic region based on digital data identifying the chromatin state comprises determining an information content for each chromatin state associated with the genomic region in the at least two groups of cells, and the method further comprises evaluating the information content for each chromatin state associated with each genomic region of the at least one genomic region in the at least two groups of cells to identify a pattern in occurrence of chromatin states and/or patterns of occurrence in chromatin states at genomic regions, and outputting an identification of each identified pattern.

In a further embodiment, in the method of any one or more of the foregoing embodiments, the method further comprises identifying the presence of the identified pattern in another genomic region of the same genome or a different genome.

In another embodiment, in the method of any one or more of the foregoing embodiments, the method further comprises identifying the absence of the identified pattern in another genomic region of the same genome or a different genome, thereby differentiating said another genomic region from the genomic region with the identified pattern.

In a further embodiment, in the method of any one or more of the foregoing embodiments, said another genomic region comprises non-transcribed gene(s), and the genomic region with the identified pattern comprises transcription start sites of transcribed gene(s).

In another embodiment, in the method of any one or more of the foregoing embodiments, the method further comprises ranking the at least one genomic region based at least in part on the information content determined for each genomic region and outputting a ranked listing of the at least one genomic region.

In a further embodiment, in the method of any one or more of the foregoing embodiments, the method further comprises outputting, for display, at least one graphic for the at least one genomic region, wherein the at least one graphic indicates, for each genomic region of the at least one genomic region, the information content for the chromatin state for the genomic region.

In another embodiment, in the method of any one or more of the foregoing embodiments, the chromatin characteristics with which chromatin states are associated comprise epigenomic characteristics that affect functional and/or activity state of one or more genes within the genomic region.

In a further embodiment, in the method of any one or more of the foregoing embodiments, the chromatin characteristics with which chromatin states are associated comprise binding interaction of transcription factors associated with genomic regions.

In another embodiment, in the method of any one or more of the foregoing embodiments, the chromatin characteristics with which chromatin states are associated comprise histone tail modifications associated with a genomic region.

In further embodiment, there is provided a method comprising any combination of one or more acts included in any one or more of the foregoing embodiments.

In another embodiment, there is provided at least one computer-readable storage medium having encoded thereon executable instructions that, when executed by at least one processor, cause the at least one processor to carry out the method of any one or more of the foregoing embodiments, or any combination of acts included in any one or more of the foregoing embodiments.

In a further embodiment, there is provided an apparatus comprising at least one processor and at least one storage medium having encoded thereon executable instructions that, when executed by the at least one processor, cause the at least one processor to carry out the method of any one or more of the foregoing embodiments, or any combination of acts included in any one or more of the foregoing embodiments.

The foregoing is a non-limiting summary of the invention, which is defined by the attached claims.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings.

DETAILED DESCRIPTION

Figure 1:
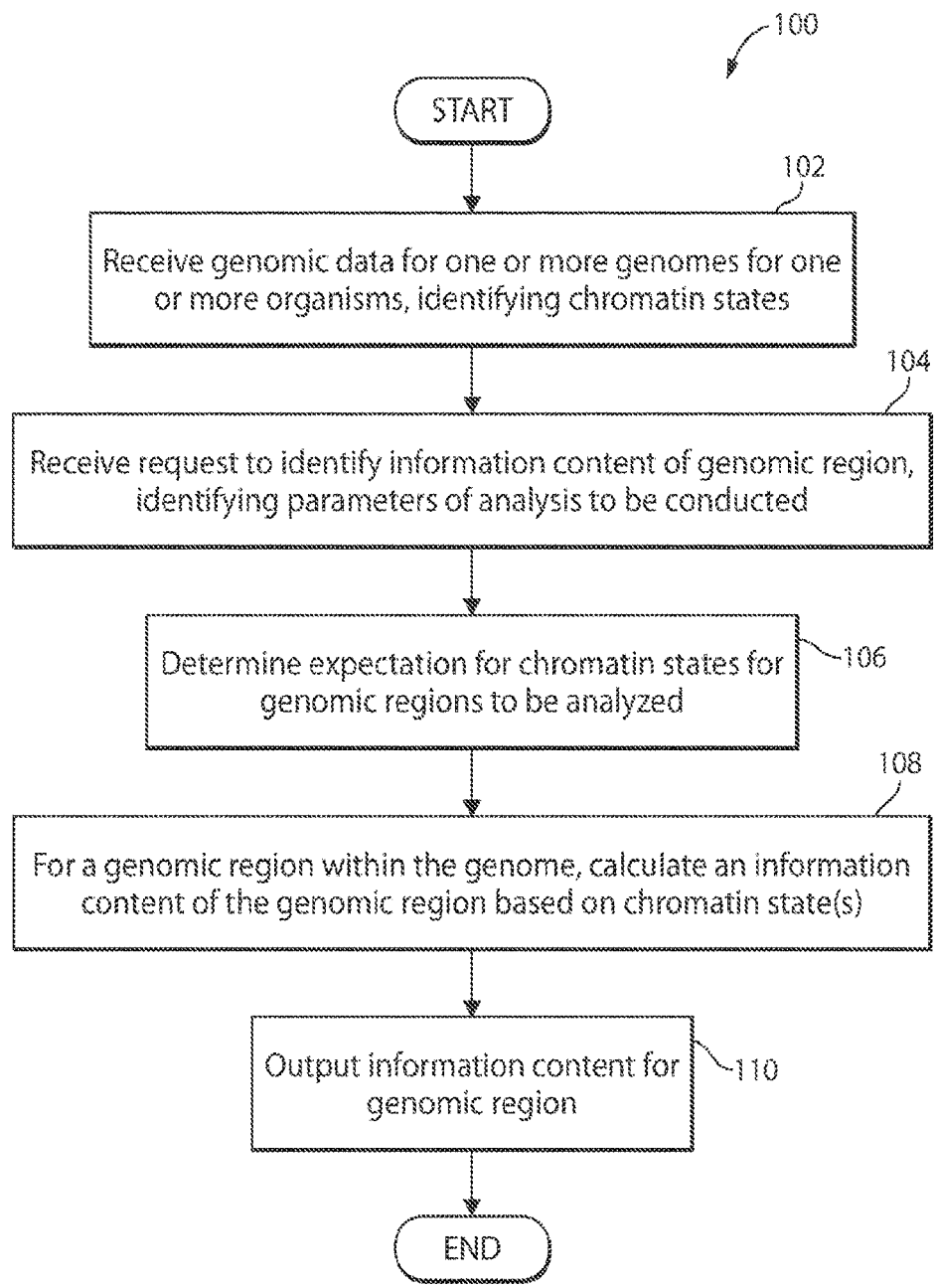
FIG. 1 is a flowchart of a technique that some embodiments may implement to perform an information-theoretic analysis of genomic regions using chromatin state data.

Described herein are embodiments of techniques for analyzing one or more genomic regions of a genome of an organism. In some embodiments, data about a genomic region may be analyzed to determine an information content of the genomic region, which may indicate an amount of information provided by the genomic region. The data about the genomic region may be or include data identifying a chromatin state for the genomic region. A chromatin state may be one of a set of chromatin states that may be associated with a genomic region and that each define a different set of one or more chromatin characteristics. Such chromatin characteristics may be structural and/or functional features of genomic regions. A chromatin state of a genomic region may be determined from, and/or describe, the genomic region such that when a genomic region has a set of one or more chromatin characteristics, a chromatin state (from the set of chromatin states) associated with that combination of one or more chromatin characteristics is identified for the genomic region. In some embodiments, based on the chromatin state, an information content may be determined that identifies an amount of information set out for the genomic region by the chromatin state for the genomic region.

The inventors have recognized and appreciated that research into genomes is limited by the complexity of analysis caused by the sheer volume of data. For a standard nucleic acid, there may be over 3 billion data points to analyze. This complexity increases when accounting for variation between organisms of a species or between cells (e.g., from different tissues) of a particular organism, which may be due in part to variation in the epigenomes of the organisms and the cells. Though cells in an organism generally or most likely have highly similar DNA sequences (except, e.g., when some cells may be mutated), other molecules associated with the DNA, such as bound to the DNA—collectively known as the epigenome—do vary between cells (e.g., of different tissues such as a heart cell vs. a brain cell). These other molecules may affect how the DNA is used in a cell, such as by affecting whether and how a gene expresses in a particular cell of a particular organism, e.g., whether a gene is switched on or off, whether a gene is translated into protein or remains silent, and/or whether certain regulatory control elements, such as enhancer elements, are active. By affecting whether and how genes express in particular cells, there can be variation in cell behavior and/or function within an organism despite having the same DNA. For every cell type of an organism, the variations in epigenome present another dimension to genomic data to consider; variations between organisms in a species provide even more genomic data to consider.

The vastness of this information complicates the task of identifying genomic regions that are good candidates for research and analysis, such as for identifying potential effects of pharmaceuticals on patients or on identifying links between diseases and genomes or genomic regions. The inventors have further recognized and appreciated that this volume of data renders manual analysis in a timeframe practical for research or other purposes impossible. Such a manual analysis would likely take many thousands of years. Moreover, while computer-implemented techniques have been previously developed for analyzing data for nucleic acids, the inventors have recognized and appreciated that this volume of data overwhelms these prior computer-implemented techniques and thus cannot be reasonably processed using them. For example, existing computer-implemented techniques for analyzing genomic data for nucleic acids cannot, within a period of time practical for research or other purposes, provide a completed analysis of epigenomic data.

The inventors have therefore recognized and appreciated the desirability of computer-implemented techniques that provide different approaches to analyzing data on genomic regions of a genome.

The inventors have recognized and appreciated the advantages that may be offered by using information theory techniques to analyze genomic information and thereby identify genomic regions of interest within a genome. More particularly, the inventors have recognized and appreciated the desirability of techniques for determining an information content of a genomic region. Determining an information content of a genomic region may include evaluating a probability of occurrence of a value associated with the genomic region, such as by evaluating the probability of occurrence in connection with an expectation of occurrence of the value. The information content on a genomic region may be used in a variety of ways, as discussed below. For example, the inventors have recognized and appreciated that genomic regions having a high information content may be the most promising candidates for research and analysis. This may be because such genomic regions may have a high information content through having content following some potential pattern or relationship rather than being or appearing merely statistically random. That potential pattern or relationship may be potentially interesting for research or analysis, or potentially more interesting than other genomic regions that have content that is or appears to be more statistically random.

The inventors have further recognized and appreciated the advantages that may be offered by using a meta-analysis of data regarding genomic regions, by analyzing data that describes a genomic region or attributes of a genomic region. Specifically, the inventors have recognized and appreciated the value of associating genomic regions with chromatin states and analyzing chromatin state data for a genomic region, rather than directly analyzing the multitude of data regarding a genomic region. The inventors recognized and appreciated that such chromatin states may be identified through defining chromatin states as combinations of chromatin characteristics, which may be structural and/or functional features of a genomic region. The inventors have recognized that each genomic region may be associated with many different structural or functional features that could qualify as chromatin characteristics, and that including each of these features as potential chromatin characteristics may lead to a large number of chromatin states, to account for potential combinations of values of these chromatin characteristics. Such a large number of states may complicate analysis. The inventors have therefore recognized and appreciated the advantages of identifying a set of chromatin characteristics that are clearly associated with structural and/or functional variation between genomic regions, such as chromatin characteristics that have distinct structural attributes or functional purposes in a genomic region. By identifying only these chromatin characteristics, a limited set of chromatin states may be identified and used for analysis.

The inventors have further recognized and appreciated the advantages of using the information theory techniques described herein in connection with a meta-analysis using chromatin states, as also described herein. Specifically, information theory techniques may be used with data indicating chromatin states of genomic regions, to identify an information content of chromatin states for a genomic region and/or an information content of the genomic region.

Those skilled in the art will appreciate that an information content of a genomic region, determined using information theory techniques from one or more chromatin states, may indicate an amount of information by evaluating a probability of occurrence of chromatin state(s) of the genomic region in connection with an expectation of occurrence (e.g., expected probability of occurrence) for chromatin state(s) for a genomic region. The expectation may be based merely on a random assortment of one or more chromatin states. Alternatively, the expectation may reflect some known information about chromatin states or about chromatin states for a particular circumstance, such as for an organism or for a genomic region or set of genomic regions. For example, the expectation may be determined from chromatin states that appear in a sample of a genome for an organism, in which a genomic region being analyzed appears. As another example, the expectation may account for known relationships in occurrence of chromatin states (e.g., chromatin states that often appear together or do not appear together) for a particular organism or for a set of genomic regions. The expectation may further account for known or unknown relationships in occurrence of chromatin states between epigenomes of various sources, e.g., cell types, organisms, species, etc. The information content may express a deviation from this expectation of the chromatin state(s) for a genomic region.

Described below are various examples of techniques for analyzing a genomic region using information theory techniques in connection with chromatin state data for the genomic region. Different examples of techniques for determining an information content, or for determining a chromatin state or chromatin characteristics are described. In addition, examples of ways in which an information content of a genomic region may be used, such as in a comparison with information content for other genomic regions or for the genomic region for other organisms, are also described. It should be appreciated, however, that embodiments are not limited to operating in accordance with any of the specific examples below, as other embodiments are possible.

A genome is an organism's complete set of DNA, including all of its genes. Each genome describes how to build and maintain that organism. In humans, a copy of the entire genome—more than 3 billion DNA base pairs—is contained in all cells that have a nucleus. Genomes vary widely in size: the smallest known genome for a free-living organism (a bacterium) contains about 600,000 DNA base pairs, while human and mouse genomes have some 3 billion DNA base pairs. Except for mature red blood cells, all human cells generally contain a complete genome. The genome includes both the coding and non-coding sequences of DNA.

The genomes of prokaryotes are contained in single chromosomes, which are usually circular DNA molecules. In contrast, the genomes of eukaryotes are composed of multiple chromosomes, each containing a linear molecule of DNA. Although the numbers and sizes of chromosomes vary considerably between different species (e.g., human cells have 23 pairs of chromosomes), their basic structure is generally the same in all eukaryotes. The DNA of eukaryotic cells is tightly bound to small basic proteins (histones) that package the long DNA in an orderly way in the cell nucleus.

While a genome contains a complete assembly of DNA, an epigenome is made up of chemical agents and/or proteins that are associated with DNA (e.g., attached to) and direct actions such as turning genes on or off, controlling the synthesis of proteins in particular cells. Such chemical agents may be natural components of the organism in which they are found and made by that organism, or may come from an external source, e.g., natural sources such as food and others from man-made sources like drugs or pesticides.

When epigenomic agents associate with DNA and modify its function, they are said to have "marked" the genome. These marks do not change the sequence of the DNA, but rather, change the way cells use the DNA information. The epigenome generally marks the genome in two main ways, both of which play a role in turning genes on or off. The first type of mark, called DNA methylation, directly affects the DNA in a genome. In this process, proteins attach chemical tags called methyl groups to the bases of the DNA molecule in specific places. The methyl groups turn genes on or off by affecting interactions between the DNA and other proteins. In this way, cells can remember which genes are on or off. The second kind of mark, called histone modification, affects DNA indirectly. DNA in cells is wrapped around histone proteins, which form spool-like structures that enable DNA's very long molecules to be wound up neatly into chromosomes inside the cell nucleus. Proteins can attach a variety of chemical tags to histones. Other proteins in cells can detect these tags and determine whether that region of DNA should be used or ignored in that cell.

The complexes between eukaryotic DNA and proteins are called chromatin, which can typically contain about twice as much protein as DNA. The major proteins of chromatin are the histones—small proteins containing a high proportion of basic amino acids (arginine and lysine) that facilitate binding to the negatively charged DNA molecule. There are five major types of histones—called H1, H2A, H2B, H3, and H4—which are very similar among different species of eukaryotes. In addition, chromatin contains an approximately equal mass of a wide variety of non-histone chromosomal proteins. There are more than a thousand different types of these proteins, which are involved in a range of activities, including, e.g., DNA replication and gene expression. Histones are not found in eubacteria (e.g., E. coli), although the DNA of these bacteria is associated with other proteins that presumably function like histones to package the DNA within the bacterial cell. Archaebacteria, however, do contain histones that package their DNAs in structures similar to eukaryotic chromatin.

The structure of the chromatin is highly cell-type-specific, providing an important additional layer of gene regulation.

Recent genome-wide studies have identified the configuration of chromatin states with high resolution in diverse cell-types, and shown that genome-wide transcriptional levels are highly correlated with chromatin-state switches. Even within the same cell-type, chromatin-state switches are closely involved in fine-tuning gene-expression patterns in a developmental stage-specific manner. Thus, chromatin state plays an important role in establishing cell identity during development.

As used herein, the term "genomic region" refers to at least a length portion of a chromosome. The length portion can be determined based on a user's preference. In some embodiments, a genomic region can comprise a nucleotide sequence encoding one or a group of genes located within a chromosome. In some embodiments, a genomic region can comprise a nucleotide sequence encoding one or a group of genes associated with at least one or more biological or cell functions, and/or epigenomic agents associated with (e.g., attached to) the nucleotide sequence. A genomic region may be a nucleosome. In some embodiments, a genomic region can comprise a nucleotide sequence encoding one or a group of genes associated with at least one binding site for a specific target (e.g., transcription factor(s)), and/or epigenomic agents associated with the nucleotide sequence. In some embodiments, a genomic region may be or include a number of base-pairs of a nucleic acid alone or together with epigenomic agents associated with the base-pairs.

As used herein, the term "epigenome" refers to molecules and/or chemical functional moieties that can associate with (e.g., attach to) DNA of a selected genomic region and/or associated histones. In some embodiments, the molecules and/or chemical functional moieties that associate with DNA of a selected genomic region and/or associated histones can affect directly or indirectly whether one or more genes within the genomic region should be turned on or off.

As discussed above, chromatin states may be associated with different sets of one or more chromatin characteristics, and chromatin characteristics may be associated with structural and/or functional features of genomic regions. The structural and/or functional features may be structural and/or functional features of a genomic region of a nucleic acid, such as structural or functional features of a segment of a nucleic acid like a gene or a set of base-pairs (e.g., a set of 200 base-pairs or other number of base-pairs). The structural and/or functional features of a genomic region may additionally or alternatively be associated with an epigenome and molecules of an epigenome, which may be also associated with a segment of a nucleic acid. Chromatin characteristics may additionally or alternatively include quantifiable events along a genome or a genomic region. Examples of such quantifiable events can include, but are not limited to histone tail modification events, DNA methylation events, transcription factor binding events, chromatin regulator binding events, higher-order chromatin folding/structure (e.g., association with the nuclear lamina, replication timing, frequency of interactions with other genomic loci), physical DNA characteristics (e.g., bendability), and DNA sequence characteristics (e.g., G/C-content (out of nucleotides A, C, G, T), sequence motif occurrence). Those skilled in the art will appreciate, however, that these are only examples and that other structural and/or functional features of genomic regions may be used. It should be further appreciated that any one or more of the foregoing examples may be used in embodiments, as embodiments are not limited to being implemented with any specific example or to any specific combination of the examples.

FIG. 1 illustrates an example of a process that may be implemented in some embodiments for analyzing genomic data for a genome of an organism (which may include the epigenome of the organism). The process 100 of FIG. 1 may be performed by an analysis facility, which may be implemented as executable instructions that are stored and/or executed by one or more computers. The computer(s) may, in some cases, be physical and/or virtual computers arranged to function as part of a service for providing analysis of genomic information remote from a user for whom the analysis is to be performed, and that may communicate with the user via one or more communication networks including, for example, the Internet. In other cases, the computer(s) may be directly operated by the user for whom the analysis is to be performed. It should be appreciated that the computer(s) may alternatively be arranged in any other manner, as embodiments are not limited in this respect.

The process 100 of FIG. 1 begins in block 102, in which the analysis facility receives genomic data for one or more genomes for one or more organisms. The genomic data that is received may be digital data, formatted for use by the analysis facility executing on one or more computers. The genomic data may include data identifying, for genomic regions, chromatin states associated with the genomic regions. In some embodiments, the chromatin states associated with the genomic regions can be identified in the database, e.g., by text description of each chromatin state, or by use of colors, numbers, symbols, or a combination thereof, assigned to each chromatin state.

The genomic data may include data for one type of cell of an organism, and/or for one organism, and/or for one type of organism. A type of organism may be, for example, a species, a gender of a species, a healthy member of a species or a member of a species having one or more conditions or diseases, or an organism having other factors that may be used to differentiate organisms. A type of cell may be, for an organism, a category of cell within an organism such as a cell having a structure and/or function distinct from other cells. Cells of different organs or different tissues, or different cells within an organ that perform different functions, may be different types of cells. Stated another way, cells with different phenotypes are considered as different cell types. Cells can be derived from tissue samples, clinical biopsies, and/or cultured cells. In some embodiments, cells can be derived from a subject to be diagnosed of a medical condition.

As used herein, the term "cell" refers to a biological cell comprising a genome. For example, cells include, but are not limited to, animal cells, plant cells, insect cells, and worm cells. In some embodiments, a cell is a eukaryotic cell. The biological cell can be a normal cell, a mutant cell, or a diseased cell. For example, a diseased cell can be a cancer cell. In some embodiments, cells can be mammalian cells including, without limitation, primate cells, human cells, and cells from any mammal of interest, including without limitation, mouse, hamster, rabbit, dog, cat, domestic animals, such as equine, bovine, murine, ovine, canine, and feline. In some embodiments, the cells can be derived from a human subject. In other embodiments, the cells are derived from a domesticated animal, e.g., a dog or a cat. Exemplary mammalian cells include, but are not limited to, stem cells (e.g., naturally existing stem cells or derived stem cells), cancer cells, progenitor cells, immune cells, blood cells, fetal cells, and any combinations thereof. The cells can be derived from a wide variety of tissue types without limitation such as; hematopoietic, neural, mesenchymal, cutaneous, mucosal, stromal, muscle, spleen, reticuloendothelial, epithelial, endothelial, hepatic, kidney, gastrointestinal, pulmonary, cardiovascular, T-cells, and fetus. Stem cells, embryonic stem (ES) cells, ES-derived cells, induced pluripotent stem cells, and stem cell progenitors are also included, including without limitation, hematopoietic, neural, stromal, muscle, cardiovascular, hepatic, pulmonary, and gastrointestinal stem cells. Yeast cells may also be used as cells in some embodiments described herein. In some embodiments, the cells can be ex vivo or cultured cells, e.g. in vitro. For example, for ex vivo cells, cells can be obtained from a subject, where the subject is healthy and/or affected with a disease. While cells can be obtained from a fluid sample, e.g., a blood sample, cells can also be obtained, as a non-limiting example, by biopsy or other surgical means know to those skilled in the art. It should be further appreciated that any one or more of the foregoing examples may be used in embodiments, as embodiments are not limited to being implemented with any specific example or to any specific combination of the examples.

In some embodiments, the genomic data may indicate a chromatin state for one genomic region within one type of cell for one type of organism, or may indicate a chromatin state for each genomic region within one type of cell for one type of organism, or may indicate a chromatin state for each genomic region within each type of cell of a group of types of cells within an organism, and so on.

As should be appreciated from the foregoing, a "chromatin state" may refer to an arrangement of chromatin, or a state of interaction between at least a portion of DNA and epigenomic molecules (e.g., proteins). Chromatin states can be determined, in part, based on chromatin characteristics described herein. Examples of chromatin states include, but are not limited to active transcription start sites (TSS), flanking active TSS, transcription at gene 5' and 3', strong transcription, weak transcription, genic enhancers, enhancers, ZNF genes and repeats, heterochromatin, bivalent/posied TSS, flanking bivalent TSS/Enhancer, bivalent enhancer, repressed Polycomb, weak repressed Polycomb, and quiescent/low. Various chromatin states have been identified in cells of different species, e.g., human. For example, distinct chromatin states in human cells are described, e.g., in Ernst and Kellis, "Discovery and characterization of chromatin states for systematic annotation of the human genome" Nature Biotechnology (2010) 28: 817-825, and Baker, "Making sense of chromatin states," Nature Methods (2011) 8: 717-722. It should be further appreciated that any one or more of the foregoing examples may be used in embodiments, as embodiments are not limited to being implemented with any specific example or to any specific combination of the examples.

Chromatin can exist in different states as chromatin can re-arrange from one state to another. By way of example only, chromatin can re-arrange from a condensed state to a transcriptionally accessible state, allowing transcription factors or other DNA binding proteins to access DNA and control gene expression. As discussed above, chromatin is the complex of DNA and proteins that are packed within the nucleus of eukaryotic cells. To form chromatin, DNA is tightly condensed by being wrapped around nuclear proteins called histones. This repeating DNA-histone complex, which consists of 146 base pairs of double-stranded DNA wrapped around eight histone proteins, is called a nucleosome. In general, the more condensed the chromatin, the harder it is for transcription factors and other DNA binding proteins to access DNA and perform their duties. When chromatin is tightly packed, and not actively being transcribed, the chromatin state is called heterochromatin. When chromatin is more loosely packed, and therefore accessible for transcription, the chromatin state is called euchromatin. Epigenetic modifications to histone proteins such as methylation/demethylation and acetylation/deacetylation can alter the structure of chromatin resulting in transcriptional activation or repression.

In other embodiments, the genomic data may indicate chromatin states for one genomic region within multiple types of cells for one type of organism. This may be useful where patterns in chromatin state for a specific genomic region, across different types of cells for one organism, are being investigated. Such patterns may arise, for example, as patterns in epigenomic data for a genomic region and, as such, data indicating a chromatin state for a genomic region across different cell types may be useful.

In still other embodiments, the genomic data may indicate a chromatin state for multiple genomic regions for one type of cell for one organism or one type of organism. For example, the genomic data may indicate a chromatin state, for each genomic region within a nucleic acid for a particular cell type, based on chromatin characteristics associated with the genomic region in the cell type.

In other embodiments, the genomic data may indicate a chromatin state for multiple genomic regions for multiple different types of cells for one organism or one type of organism. For example, the data may indicate a chromatin state for each of multiple types of cells across multiple or all regions of a nucleic acid, based on chromatin characteristics associated with the genomic region in the cell type.

In further embodiments, the genomic data may indicate a chromatin state for multiple different types of cells and multiple different organisms or types of organisms, which may be the case when genomes of organisms or types of organisms are to be compared, as discussed below.

The chromatin state associated with a genomic region and/or cell type may be identified in any suitable manner in the genomic data, as embodiments are not limited in this respect. In some embodiments, the chromatin state may be explicitly stated in the genomic data. In some such embodiments, the chromatin state may be explicitly identified with an identifier, which may be an alphanumeric identifier (e.g., alphabetic, numeric, or both) or other identifier. The identifier may, in some cases, be a color or be associated with a color. In other embodiments, the chromatin state may not be explicitly stated in the genomic data, but may be determinable from the data. For example, chromatin characteristics for genomic regions (and for one or more cells, etc.) may be included in the genomic data. From the chromatin characteristics, chromatin states may be determined. In such embodiments, as part of the process 100 (while not illustrated in FIG. 1), the analysis facility may determine chromatin state data for different genomic regions. It should be further appreciated that any one or more of the foregoing examples may be used in embodiments, as embodiments are not limited to being implemented with any specific example or to any specific combination of the examples.

The analysis facility may receive the genomic data in block 102 in any suitable manner. In some embodiments, the genomic data may be received via a network, having been transmitted by a user or by a device operated by a user for whom the analysis is to be performed. The genomic data may also be received from a data store accessible to the analysis facility, such as a data store of a computer on which the analysis facility is executing or a data store accessible to the analysis facility via a network. Accordingly, receiving the genomic data may include transmitting and/or receiving one or more messages over one or more communication lines, which may be or include lines (e.g., buses) within a computing device or one or more links of one or more wired and/or wireless computer networks, including the Internet.

In block 104, the analysis facility may additionally receive a request to identify information content of one or more genomic regions, identifying parameters of an analysis to be conducted. The request may be received from a user or other entity. The request may identify a manner in which an analysis is to be performed.

For example, if an analysis is to be performed of only a portion of the genomic data received in block 102, the request may identify the portion. The request may identify that only a genomic region or a specific set of genomic regions are to be analyzed. As another example, the request may identify that a specific type of cell, or a set of specific types of cells are to be analyzed, or that data for a particular organism or type of organism is to be analyzed.

The request may additionally or alternatively identify a desired output of an analysis. For example, in some embodiments a calculation of information content for each of one or more genomic regions is desired, and the desired output may be merely calculation and storage of the values. Other outputs may additionally or alternatively be requested, such as a visualization of information content or an analysis of information content with respect to at least part of a genome for different organisms or different types of organisms (e.g., a comparative analysis).

The request may additionally or alternatively identify parameters of an information theory analysis to be performed on data, such as a source of data on which to identify an expectation for chromatin state. As discussed above and in further detail below, the expectation for chromatin state may be used to determine an information content of a particular set of chromatin states for a genomic region, as the information content may be based in part on whether and how a chromatin state varies from an expectation. Adjusting how the expectation is determined may therefore adjust an information content that is calculated for a genomic region.

Accordingly, in some embodiments, a request may identify the data on which to base a determination of an expectation for chromatin states. For example, the request may identify that an expectation for occurrence of a chromatin state is to be determined as a uniform probability for each of the possible chromatin states (i.e., for n chromatin states, a probability of occurrence of 1/n). As another example, the request may identify that an expectation for occurrence of a chromatin state is to be determined from an observed occurrence of the chromatin state in genomic data. The observed occurrence may be determined from genomic data received in block 102, or some portion of it, or may be determined using other genomic data, such as previously-received genomic data for one or more types of cells, one or more organisms, or one or more types of organisms. As a further example, the request may identify that an expectation for occurrence of a chromatin state may be determined from relationships identified in chromatin states, such as relationships in occurrence of chromatin states. For example, if two chromatin states are observed to appear together often in genomic data, a relationship in occurrence may be observed. The relationships may be determined from genomic data received in block 102, or some portion of it, or may be determined using other genomic data, such as previously-received genomic data for one or more types of cells, one or more organisms, or one or more types of organisms.

While various types of information have been described as potentially being included in a request, it should be appreciated that embodiments are not limited to receiving the information in a request, and not limited to receiving the information. In some other embodiments, an analysis facility may be pre-configured with some of the information described as being received in the request. For example, with respect to determining an expectation, in some embodiments an analysis facility may be pre-configured to determine an expectation in a particular manner. As another example, with respect to an output, in some embodiments the analysis facility may be pre-configured to generate a particular type of output.

In block 106, the analysis facility determines an expectation for chromatin states to be analyzed, as identified in the request. The expectation for the chromatin states may be determined in block 106 through retrieving a previously-calculated expectation from a data store, or through newly calculating the expectation. For example, in embodiments in which the expectation is to be calculated in a certain manner from at least a portion of the genomic data received in block 102, in block 106 the analysis facility may review the genomic data to determine the expectation. Examples of ways in which the analysis facility may determine an expectation for use in determining an information content are described in detail below.

In block 108, the analysis facility calculates an information content of each genomic region for which an analysis is to be performed, based on genomic data received in block 102. Calculating the information content for a genomic region may include calculating an information content for each chromatin state associated with that genomic region in the genomic data to be analyzed. The analysis facility may calculate the information content in block 108 based on parameters with which the analysis facility is pre-configured or that were identified in a request received in block 104, as discussed above. Such parameters may relate, as discussed above, to which genomic regions are to be considered and how an expectation is to be determined.

For example, in some embodiments an information content may be calculated that indicates a value related to a Shannon uncertainty of a chromatin state for a genomic region. Exemplary techniques for determining the value related to the Shannon uncertainty are discussed in detail below. In brief, the value may indicate how much "information" is provided by the chromatin state(s) of the genomic region by indicating how much the chromatin states vary from what would be expected of a purely random assortment of chromatin states. Determining the information content may include evaluating a probability of occurrence of a chromatin state at the genomic region. An expectation for a chromatin state may be determined as a uniform probability for each chromatin state (i.e., for n chromatin states, a probability of occurrence of 1/n). The information content may be calculated with the probability of occurrence of the chromatin state and the uniform probability for expectation of occurrence.

As another example, in some embodiments an information content may be calculated using a technique based on Kullbeck-Leibler divergence. A Kullbeck-Leibler divergence indicates how much chromatin states vary from an expectation that is based on a population being analyzed. Accordingly, in such a process, an expectation may be determined from an analysis of genomic data, such as an analysis of the genomic data or a part of the genomic data received in block 102. For example, the analysis facility may determine an observed occurrence of each chromatin state in the genomic data and determine an expectation for occurrence of the chromatin state from the observed occurrences.

Exemplary techniques for determining an information content using a Kullbeck-Leibler divergence technique are discussed in detail below.

As a further example, in some embodiments an information content may be determined based on relationships in occurrence between chromatin states and/or between chromatin states and genomic regions. Some techniques for calculating an expectation for use with a Kullbeck-Leibler divergence may provide an expectation that is in some ways tailored to a population (e.g., determined from the genomic data received in block 102 and thus tailored to that genomic data). However, observing occurrences of chromatin states may assume independence between chromatin states and therefore not account for relationships in occurrence between states. If two states always occur proximate to one another in genomic regions, or if a genomic region includes, in multiple different cell types, a same chromatin state, these relationships in occurrence may impact an expectation. Accordingly, in some embodiments an information content may be calculated based on relationships in occurrence between chromatin states and/or between chromatin states and genomic regions. Examples of such techniques are discussed in detail below.

As part of determining an information content in block 108, an analysis facility may perform various additional steps, as identified in the request for block 104. As discussed above, a request may identify a desired output of the analysis, such as a visualization of information content or an analysis of information content of at least part of a genome for different organisms or different types of organisms (e.g., a comparative analysis). Accordingly, in block 108, the analysis facility may perform additional steps related to the calculation of the information content to determine an output as requested in the request. For example, if a visualization is requested, a visualization based on information content may be produced in block 108. Examples of ways in which a visualization may be determined are discussed below. As another example, the analysis facility may perform a comparative analysis or otherwise evaluate information content of one or more genomic regions for one or more types of cells with respect to information content for other genomic regions or other cells. The other genomic regions/cells may be associated with another organism, another type of organism, or others. Examples of applications of information content for genomic regions are discussed below.

In block 110, once the information content or other result (e.g., visualization) is generated by the analysis facility, the information content or other result is output from the analysis facility. The output may be performed in any suitable manner. For example, the analysis facility may store the information content or other result in a data store accessible to the analysis facility. As another example, the analysis facility may display a visualization via a display. As a further example, the analysis facility may transmit information regarding the information or result via one or more communication networks to a receiver, such as by transmitting information content values for storage or by transmitting visualization data for output. Accordingly, outputting the information content or other result may include transmitting and/or receiving one or more messages over one or more communication lines, which may be or include lines (e.g., buses) within a computing device or one or more links of one or more wired and/or wireless computer networks, including the Internet.

Once the analysis facility outputs the information content or other result in block 110, the process 100 ends.

Following the process 100, information regarding information content of one or more genomic regions is available and may be used in a variety of ways. For example, the information content may be used to identify genomic regions that are candidates for further research. As another example, the information may be used to diagnose or screen a patient for a medical condition, such as in embodiments described herein in which a comparison is performed and one side of the comparison relates to a genome for a subject having or being more likely to have a medical condition. As a further example, the information may be used to identify a treatment or treatment regimen for a patient, such as by identifying a treatment or treatment regimen based on information regarding a genome of the patient and/or a comparison of the genome of the patient to a genome for a subject who was successfully or unsuccessfully treated with a particular treatment or treatment regimen.

The process 100 was described above in connection with different options and different ways in which operations may be performed. To aid in illustrating how embodiments may be implemented, specific examples of the process 100 will be briefly described.

As one specific example, genomic data for a genome of a type of organism may be evaluated. The genomic data may include data for one type of cell for the type of organism. The data may have been determined from multiple cells for a single organism or for multiple organisms of the type, as embodiments are not limited in this respect. From these cells, chromatin state data for multiple genomic regions (e.g., for an entire nucleic acid or only a portion of a nucleic acid) may be determined. The chromatin state data may indicate, for each genomic region, a chromatin state of that region for the single cell type. The data may therefore be considered to be one-dimensional, with each data point identifying a chromatin state for a genomic region in the cell type. Using the genomic data, the analysis facility may determine an information content for each genomic region and/or for the cell type. The analysis facility may determine the information content based on the chromatin state included in the genomic data for each genomic region. Thus, for a particular genomic region, the chromatin state that is associated with the cell types may be evaluated. Specifically, the relative occurrence of the chromatin state in the cell type at that genomic region may be compared to an expectation of occurrence for chromatin states. A variation between the relative occurrence of the chromatin state and the expectation for chromatin states may be used to determine the information content. As discussed above, an expectation may be determined in a variety of ways, including from an analysis of the genomic data.

As another specific example, genomic data for a genome of a type of organism may be evaluated. The genomic data may include data for multiple types of cells (e.g., more than 10 types of cells, more than 50 types of cells, or more than 100 types of cells) for the type of organism. The data may have been determined from multiple cells of each type, and may have been determined from cells for a single organism or multiple organisms of the type, as embodiments are not limited in this respect. From these cells, chromatin state data for multiple genomic regions (e.g., for an entire nucleic acid or only a portion of a nucleic acid) may be determined. The chromatin state data may indicate, for each genomic region, a chromatin state of that region for each cell type of the multiple cell types. The data may therefore be considered to be two-dimensional: X-axis data indicating genomic regions, and Y-axis data indicating cell types, with each data point identifying a chromatin state for a genomic region in a cell type. Using the genomic data, the analysis facility may determine an information content for each genomic region. The analysis facility may determine the information content based on the chromatin states (for each cell type) included in the genomic data for each genomic region. Thus, for a particular genomic region, multiple chromatin states that are individually associated with cell types are evaluated. Specifically, the relative occurrence of chromatin states in the cell types at that genomic region may be compared to an expectation of occurrence for the chromatin states. A variation between the relative occurrence of the chromatin states and the expectation for the chromatin states may be used to determine the information content. As discussed above, an expectation may be determined in a variety of ways, including from an analysis of the genomic data.

This foregoing example illustrates a case where two or more "groups" of cells may be considered. In that case, the different groups of cells are different cell types for an organism or type of organism. It should be appreciated, however, that embodiments may operate with other groups of cells. For example, the different groups of cells may be different types of organism. In one such example, genomic data may be for different organisms but all for the same cell type. An analysis may be conducted to identify an information content for each genomic region based on chromatin states associated with that genomic region across the same cell type, such as in different organisms.

As another example of two groups of cells, the two or more groups of cells may be of healthy/normal organisms of a particular type and organisms of that type that have a disease/condition. In such a case, all cells to be considered may be of a particular type or set of two or more types. As another example, the two or more groups of cells may be different organisms that each have a same disease/condition. In such a case, all cells to be considered may be of a particular type or set of two or more types. As a further example, the two or more groups of cells may be cells (of a single type or multiple types) for different genders of the same type of organism. Any suitable combination of groups of cells, from any suitable source, may be used in embodiments.

As a specific example of an output that may be generated by an analysis facility, a visualization may be produced from information content. For example, a visualization of relative information content for genomic regions may be produced. The visualization may be formatted as a bar chart, with the bar for each genomic region indicating an information content of that genomic region. In a case where multiple chromatin states associated with a genomic region are identified (e.g., for multiple cell types), a relative contribution to the information content of that genomic region by each chromatin state associated with the genomic region may be indicated in the visualization. Examples of such visualizations are discussed in detail below.

As another example of an output that may be generated by an analysis facility, an information content of genomic regions may be evaluated to identify genomic regions for which an information content meets some criteria. The criteria may be, for example, a threshold information content, such as an identification of genomic regions for which an information content is above some value. The criteria may additionally or alternatively be based on a ranking of genomic regions, such as a top 5, top 10 or other number of genomic regions based on information content. The criteria may additionally or alternatively be based on an analysis of the information contents, such as by comparing information content for genomic regions or by an identification of genomic regions satisfying some statistical value determined from the information contents. As a specific example of such statistical value, a median, standard deviation, or other value may be used, such that an identification of genomic regions having an information content more than one standard deviation away from a mean or more than two standard deviations away from a mean may be determined.

As another example, a ranking of genomic regions based on information content may be output by an analysis facility.

As a further example of output, based on information contents determined for chromatin states associated with genomic regions, the analysis facility may identify for each genomic region a "top" chromatin state. The top chromatin state may be a state that has a highest information content (e.g., highest numeric value) from among chromatin states associated with the genomic region in the genomic data to be analyzed. The analysis facility may then, as part of determining a result of the analysis, identify a sequence of top chromatin states that are associated with the genomic regions to be analyzed, with the chromatin state for each genomic region being the one with the highest information content for that genomic region. When the genomic data on which the analysis was based includes data for an organism or type of organism, such as by having data on chromatin states associated with one or more cell types for the organism or type, the sequence of chromatin states may reflect a "consensus" sequence for chromatin states for the organism or type. This may be a summary of chromatin states across the genomic regions, such as for a nucleic acid. It may be useful, for example, in summarizing epigenome data associated with segments of a nucleic acid. A "nonsensus" sequence for chromatin states for the organism or type may be similarly determined from chromatin state calls having a lowest information content for a genomic region.

As another example of output, information contents for genomic regions in two groups of cells may be compared. The two groups of cells may be any suitable groupings, including examples described above. For example, the two groups may be for different organisms, different types of organisms, or different genders. The two groups may also be associated with different characteristics of interest. For example, one group may be considered a "control group" including normal or healthy organisms of a type (e.g., normal or healthy organisms of a species) and while another may be a "test group," where the test group has or is more likely to have a particular characteristic of interest that the control group does not have or is less likely to have. The characteristic of interest may be, for example, having a medical condition, having a disease, having been exposed to a particular substance or environment, or other medically-significant characteristic. Thus, the two groups may, for example, have different medical statuses (e.g., healthy or having a particular disease). Within a group of cells, the information contents may be for a single cell type or for multiple cell types, or include any other suitable grouping of cells. One advantageous example may be where each group of cells is associated with multiple cell types for one type of organism, to identify information contents for genomic regions for that type of organism based on multiple cell types from that organism. The two types of organism may be different species, different genders, or other types. The information content data for the two groups of cells may be for the same genomic regions and the same types of cells. The analysis facility may perform the comparison for the information contents for the genomic regions to identify genomic regions that meet some criteria. For example, areas that include one or more genomic regions and for which there are large differences in chromatin states may be identified. The amount of difference in information content may be determined in various ways. For example, one way may be to calculate, for each genomic region and for each chromatin state at that genomic region in the two groups, a difference between the information content for that chromatin state at that genomic region. The sum of these differences for chromatin states may be determined to be the difference in information content for the genomic region. The analysis facility may evaluate differences in genomic regions to identify genomic regions or sets of genomic regions with large differences. Large differences may be identified as differences above a fixed threshold or by identifying, from a comparison between differences in genomic regions, differences that are statistically significant. Additional details regarding ways in which a comparative analysis of information contents for genomic regions may be performed are provided below.

In some embodiments, by identifying the difference in chromatin states associated with a genomic region between a control group and a test group, such as of a medical condition (e.g., cancer), such information can provide insights into developing a treatment or therapy, e.g., epigenetic silencing of genes, for the medical condition (e.g., cancer).

As a further example, the information content for genomic regions (which may include information contents for each chromatin state associated with a genomic region) may be analyzed to identify patterns in the chromatin states. The patterns may identify relationships in occurrence of chromatin states. The patterns may identify relationships between chromatin states and genomic regions, such as chromatin states that occur in connection with segments of nucleic acids having particular functions. The patterns may additionally or alternatively identify relationships in occurrence between chromatin states. Such relationships in occurrence may identify two or more states that occur or do not occur together. The relationship in occurrence (or non-occurrence) may be between genomic regions or types of cells, including any of the examples of genomic regions and examples of types of cells discussed above. Such relationships may therefore appear in the same genomic region in different types of cells (e.g., different cells types for one organism or one species, or the same cell type for different genders of a species or different species, etc.). Such relationships may additionally or alternatively appear in different genomic regions, such as adjacent or non-adjacent genomic regions within a genome. One specific example of such a pattern may be that for a particular cell type, a chromatin state always appears, or has a statistically higher likelihood of appearing, adjacent to another chromatin state, such as that the chromatin states appear in adjacent segments of a nucleic acid (e.g., when one chromatin state appears at a segment, the other chromatin state always appears in an adjacent segment). Another specific example is that when a chromatin state appears at a genomic region in one cell type for a species, another chromatin state always appears, or has a statistically higher likelihood of appearing, at the genomic region in a second cell type for the species. A third specific example is that when a chromatin state appears at a genomic region in one cell type, a second chromatin state never appears, or is statistically less likely to appear, at an adjacent genomic region for the cell type. Other examples of patterns in occurrence or non-occurrence of chromatin states will be appreciated from the foregoing by those skilled in the art.

The analysis to identify such patterns may be carried out using various techniques for identifying patterns in data, examples of which are described below. In one particular example described below, an Expectation Maximization technique is applied to identify local patterns, though other pattern identification techniques such as Gibbs Sampling may be used.

Examples of chromatin states that are associated with chromatin characteristics are described above. Those skilled in the art will appreciate how to determine chromatin characteristics from biological data, as well as how to determine chromatin states from chromatin characteristics. One example is provided below of a way to determine chromatin characteristics from chromatin data, to provide an illustration of ways in which other chromatin characteristics may be determined from biological data.

Chromatin mapping techniques known to an ordinary person skilled in the art can be used to determine chromatin characteristics described herein. For example, interactions of protein with DNA can be determined by a combination of chromatin immunoprecipitation (ChIP) and DNA sequencing or a hybridization array. ChIP uses antibodies to particular histone modification or DNA-binding proteins to purify associated DNA, which can then be analyzed by sequencing (e.g., massively parallel DNA sequencing) or microarrays to identify the binding sites of DNA associated proteins. Antibodies directed to unmodified histones and various distinct histone modifications (including, e.g., but not limited to H3K4me1, H3K4me3, H3K9me3, H3K27me3, H3K36me3) are commercially available. Information on additional histone modifications and corresponding antibodies can be found, e.g., in Egelhofer et al. "An assessment of histone-modification antibody quality" Nature Structural & Molecular Biology (2011) 18: 91-93, and online at http://compbio.med.harvard.edu/antibodies/.

Other epigenomics methods include, but are not limited to DNA methylation assays (e.g., restriction endonuclease based methods and bisulfite sequencing), and direct detection (e.g., single molecule real time sequencing). Additional information about epigenomics methods amenable to the methods described herein can be found, e.g., Davis et al., "Entering the era of bacteria epigenomics with single molecule real time DNA sequencing" Current Opinion in Microbiology (2013) 16(2): 192-198; Eads et al. "MethyLight: a high-throughput assay to measure DNA methylation." Oxford University Press (2000) 28 (8): 1-7; and Laird "Principles and challenges of genome-wide DNA methylation analysis." (2010) Nature Reviews", 11: 191-203.

Various statistical techniques can be applied to datasets cataloguing different chromatin marks and/or proteins, such as from different species. Non-limiting examples of statistical techniques include, but are not limited to heat map and hierarchical clustering, integrative analysis (using chromatin marks to predict function), cluster and principal component analysis, machine learning, combinatorial model considering probability of the presence of certain marks, integrative analysis of genome-wide binding maps, multivariate hidden Markov model. Additional information on use of these statistical techniques to identify chromatin states can be found, e.g., in Roudier, F. et al. EMBO J. 30, 1928-1938 (2011); Liu, T. et al. Genome Res. 21, 227-236 (2011); Gerstein, M. B. et al. Science 330, 1775-1787 (2010); modENCODE Consortium et al. Science 330, 1787-1797 (2010); Riddle, N.C. et al. Genome Res. 21, 147-163 (2011); Kharchenko, P. V. et al. Nature 471, 480-486 (2010); Filion, G. J. et al. Cell 143, 212-224 (2010); Ernst, J. & Kellis, M. Nat. Biotechnol. 28, 817-825 (2010); and Ernst, J. et al. Nature 473, 43-49 (2011).

As discussed above, in some embodiments it may be advantageous to limit a number of chromatin characteristics to be considered in determining chromatin states. There may be many different structural and/or functional features that may qualify to be evaluated as chromatin characteristics. However, with a large number of chromatin characteristics, there may be a correspondingly large number of chromatin states to consider, to account for different combinations of potential values of the chromatin characteristics. The inventors thus recognized and appreciated the advantages of a reduced number of chromatin characteristics, as well as of certain techniques for identifying characteristics to serve as chromatin characteristics.

In some embodiments, the chromatin characteristics may be manually selected. In a manual selection, a skilled artisan may evaluate potential chromatin characteristics to identify those characteristics that have a known, strong correspondence to structural or functional biological features. In addition to having a known, strong correspondence, the characteristics that are selected may be associated with distinctly different structural or functional biological features, such that the characteristics can be considered "orthogonal" to one another when considering the biological role of the characteristics. Thus, in some embodiments, when two characteristics may both have a known, strong correspondence to the same structural or functional biological feature, only one is selected. By selecting such "orthogonal" characteristics, a limited set of characteristics that have distinct known biological roles can be identified.

These characteristics having distinct known biological roles may then be associated with chromatin states. Each state may be associated with different values of the chromatin characteristics. The values may be quantitative values (e.g., numeric values with a certain range) or qualitative values, such as having values that are "low" or "high" compared to one another.

In some embodiments, the chromatin states can be assigned based on known chromatic characteristics associated with pre-determined chromatin states, e.g., as described in Ernst and Kellis, Nature Methods (2012) 9: 215-216 and Roadmap Epigenomics Consortium et al. Nature (2015) 518: 317-30.

As an alternative to a manual selection, an automated selection may be made. In such an automated selection, a classifier and feature extractor may be used to analyze genomic data about potential chromatin characteristics. The classifier and feature extractor may be configured to identify an input number of chromatin states and to identify a set of chromatin characteristics that would be associated with those states, including by identifying relationships between chromatin characteristics and biological features (e.g., structural and/or functional features). The automated analysis may identify a set of characteristics that may be considered "orthogonal" by identifying, from data, characteristics that have low correlations to one another with respect to biological features. Chromatin characteristics that have low correlations to one another may be considered orthogonal. The automated analysis may output a set of chromatin characteristics as well as a set of chromatin states. In these embodiments, known techniques for classifiers and feature extractors may be used.

Examples of Specific Techniques with which Embodiments May Operate

Described above were a number of different techniques that may be used in embodiments. Below, some specific examples are described for how these techniques may be used in some embodiments. The examples below are described in connection with an exemplary implementation termed an "epilogos" system. It should be appreciated that embodiments are not limited to operating in connection with the examples provided below.

Analysis and Visualization of Multiple Epigenomes

Described below are some methods behind a system that is identified as "epilogos." The epilogis system is configured for analysis and visualization of epigenomic chromatin state models. The epilogos system may include functionality for visualizing summaries of chromatin state calls across large numbers of epigenomes, and prioritization of regions that are most likely to be of interest for further analysis. The epilogos system may also include different functionalities for analysis of large-scale epigenomic datasets, described below.

The system is described in connection with one particular set of genomic data and chromatin states, which are associated with a chromatin state model learned using ChromHMM software, with input being 127 different epigenomes covering more than 100 distinct cell types. This chromatin state model consists of 15 states and was built in the context of the Roadmap Epigenomics Project. It utilizes ChIP-seq datasets for chromatin characteristics that are five core histone tail modifications, namely, H3K4me1, H3K4me3, H3K9me3, H3K27me3 and H3K36me3. Each of these modifications has been associated with certain functional genomic elements. Combined, they are believed to capture a large part of the epigenomic variation between cell types.

Prior Visualizations of Chromatin States Across Multiple Epigenomes

Perhaps a straightforward way of visualizing chromatin state data is through the use of the colors assigned to each chromatin state. The typical resolution of a ChromHMM chromatin state model is 200 bp. Therefore, each 200 bp-wide site can be assigned a state with its designated color. Extending this across multiple epigenomes results in a matrix of state colors, as shown in FIG. 2.

Figure 2:
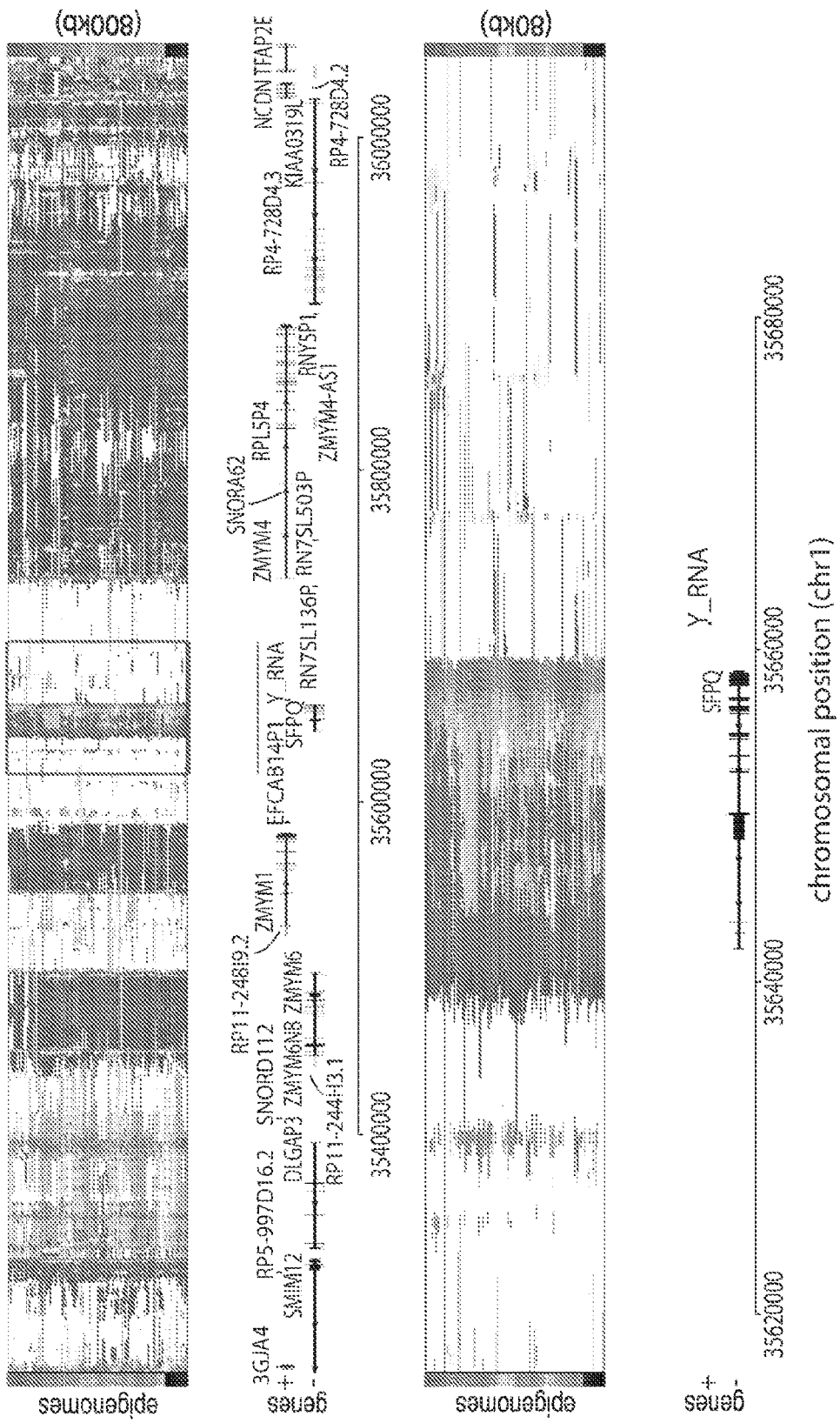
FIG. 2 is a visualization of a conventional way of visualizing epigenomic data.

FIG. 2 provides a standard depiction of chromatin states across 127 epigenomes. The top track of FIG. 2 shows an 800 kb region on chromosome 1, and the bottom track a zoomed-in smaller 80 kb region, indicated by the brown rectangle in the top track. Chromatin statea are according to the Roadmap Epigenomics Project mentioned above. Genes, in accordance with GENCODE v19, are plotted underneath both tracks. Colors left and right indicate the various epigenome cell-type groups.

The advantage of this method of visualizing chromatin state calls is that one can see exactly which states were called in which epigenome. However, the inventors have recognized and appreciated that it doesn't provide an immediately clear picture on which states or regions are the most interesting to focus on for downstream analyses.

Figure 3:
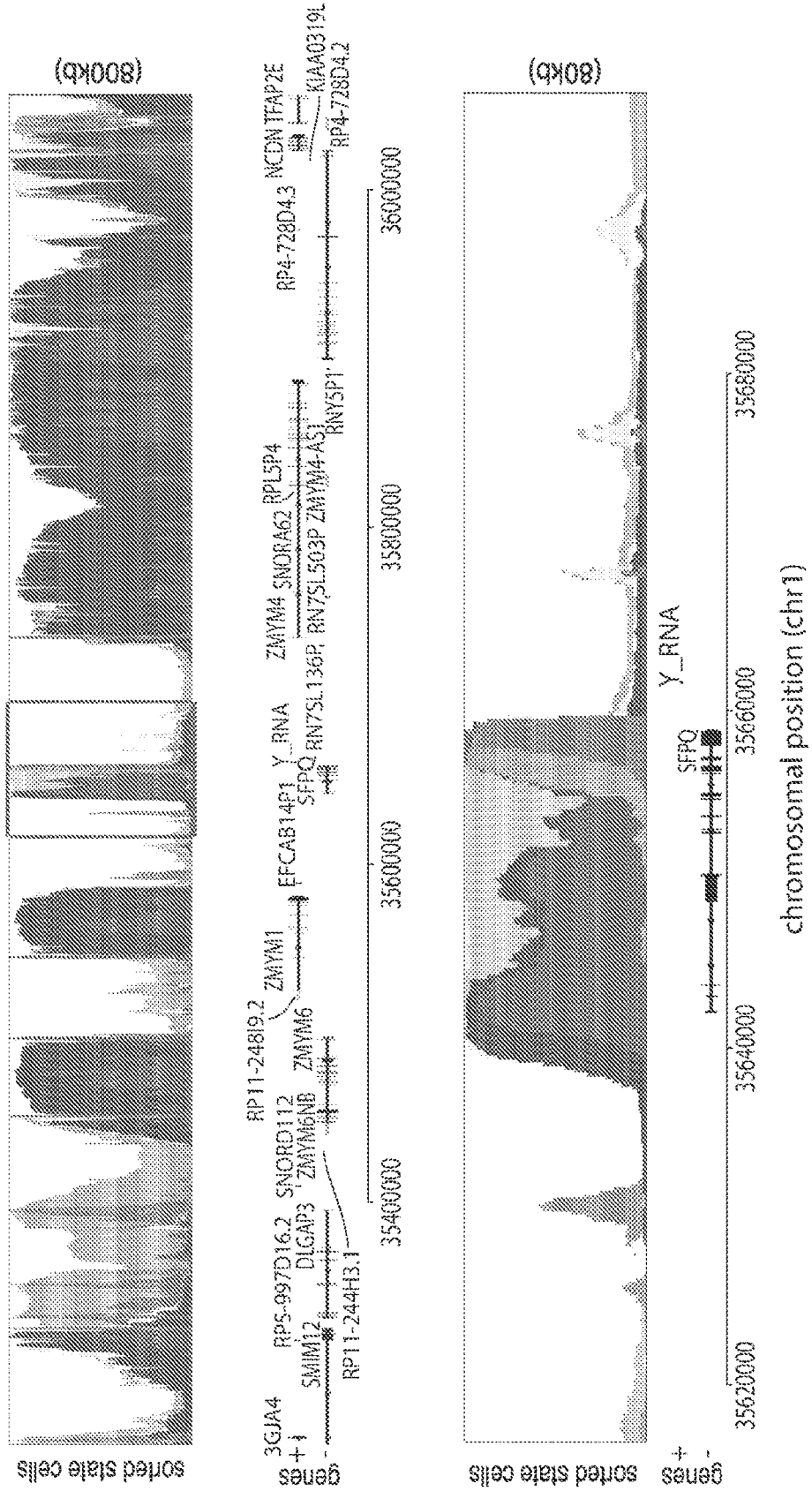
FIG. 3 is a different way of visualizing epigenomic data, as proposed herein.

The inventors have recognized and appreciated the advantages, over the visualization of FIG. 2, of a way for visualizing chromatin state calls across multiple epigenomes. An example is shown in FIG. 3. FIG. 3 shows column-wise ordered chromatin states across 127 epigenomes. The visualization is formatted as described above in connection with FIG. 2, except data are sorted row-wise, and epigenome cell-type colors are not indicated. In the visualization of FIG. 3, for each 200 bp-wide site in the genome, the associated chromatin state calls are ordered in terms of their chromatin state number, gouping all same-state calls together.

The inventors have recognized and appreciated that this visualization may provide helpful intuition on the general characteristics of a genomic region of interest, but that the visualization does not distinguish between random patterns and patterns that truly contain new information that can be used to guide follow-up analyses. As a consequence, the visualization cannot be used to prioritize genomic regions of interest.

Rather, the inventors have recognized and appreciated that a way of scoring the amount of information contained in each genomic region, and the contribution of each chromatin state towards that amount, is helpful to distinguish genomic regions of interest from random data.

Information Content of Chromatin State Calls

The field of information theory provides tools to assess the amount of information present in a collection of chromatin state calls. The inventors have recognized and appreciated that, when used in connection with chromatin state data, information theory techniques may provide for distinguishing random patterns from patterns that contain information, and thus allow for identification of the most "surprising" regions for research or other purposes.

Information content may be calculated for a set of chromatin states that are:
across multiple genomic regions for a single epigenome (e.g., a single row in FIG. 2) or
across multiple epigenomes for a single genomic region (e.g., a single column in FIG. 2).

In either case, the chromatin states can be considered to be multiple samplings from a discrete random variable X with n distinct possible values. In this case, these n possible values are the chromatin states. In general, they are referred to as symbols, collectively forming the alphabet. During a repeated sampling procedure, each member of the alphabet is drawn zero or more times.

Shannon Uncertainty

We denote the probability of occurrence of some chromatin state i∈X with Pr[X=i], or p(i) for short. The Shannon uncertainty H(X) of X is then defined as:

$$H(X) = -\sum_i p(i)\log_2(p(i)). \quad (1)$$

The Shannon uncertainty can be thought of as the average unpredictability: the higher the uncertainty, the more uniformly random the variable is. Although any logarithmic base can be used in theory, in some embodiments logarithms with base 2 are used. This allows for the amount of information to be expressed in bits.

Information Content

The information content (IC) of a variable X follows from the Shannon uncertainty by relating H(X) to the maximal possible uncertainty given the alphabet size of X (i.e., n). As an example of this, assume R to be a discrete uniformly random variable with alphabet size n and uniform probabilities $$p_i = \frac{1}{n}.$$

Because of its complete unpredictability, uniform randomness results in the highest possible uncertainty. Using the notation from H(X) above, the uncertainty for R, and therefore also the maximal uncertainty for X, is thus:

$$H(R) = H\max(X) \quad (2)$$

$$= -\sum_i \frac{1}{n}\log_2\left(\frac{1}{n}\right) \quad (3)$$

$$= \sum_i \frac{1}{n}\log_2(n) \quad (4)$$

$$= \log_2(n). \quad (5)$$

The information content IC(X) of X is obtained by subtracting H(X) from H max(X):

$$IC(X) = H\max(X) - H(X) \quad (6)$$

$$= \log_2(n) + \sum_i p(i)\log_2(p(i)). \quad (7)$$

By defining $$v = \frac{1}{n}$$

the uniformly random probability for alphabet size n, the above can be rewritten as:

$$IC(X) = -\sum_i p(i)\log_2(v) + \sum_i p(i)\log_2(p(i)) \quad (8)$$

$$= \sum_i p(i)\log_2(p(i)) - \sum_i p(i)\log_2(v) \quad (9)$$

$$= \sum_i p(i)\log_2\left(\frac{p(i)}{v}\right). \quad (10)$$

which shows the observed probabilities p(i) are compared to an "expected" uniformly random probability v.

Visualization of Information Content

Figure 4:
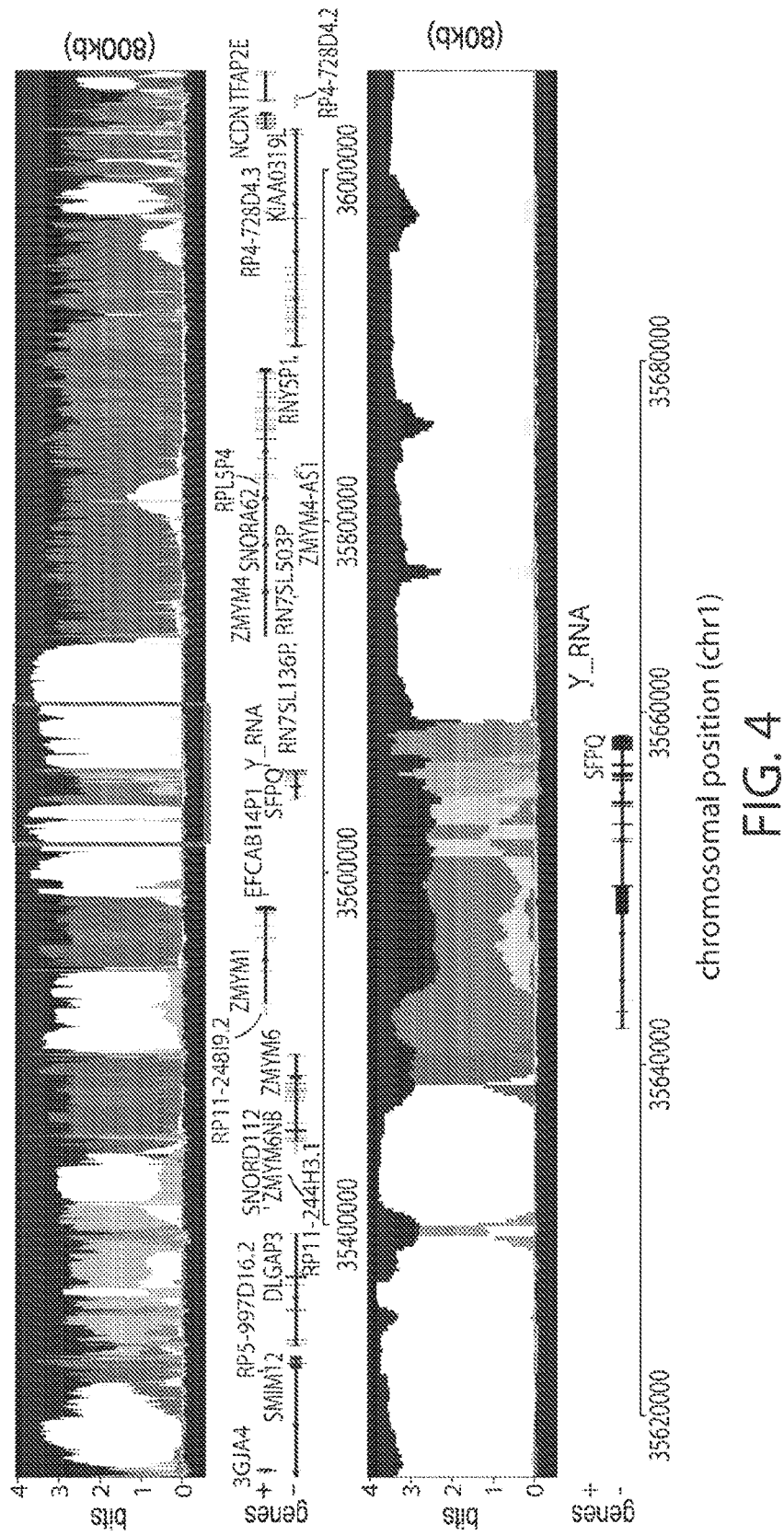
FIG. 4 is a visualization of epigenomic data produced using information theoretic analysis in accordance with some techniques described herein.

As discussed above, an observed set of chromatin states across m epigenomes for a single 200 bp genomic region can be regarded as m samplings from a random variable X with n possible distinct values. The information content IC(X) for a single genomic region can be visualized by displaying a stack of all chromatin states occurring at a genomic region. The total height of the stack is IC(X), and the chromatin states may be ordered in the stack by their frequency of occurrence at that position. The height of each individual chromatin state i is set to be p(i)IC(X) (as shown in FIG. 4). An example of such a visualization is shown in FIG. 4. The visualization of FIG. 4 is formatted in the manner described above in connection with FIG. 2. The data of FIG. 4 was created from 127 epigenomes for a single genome.

The visualization has the advantage of emphasizing for each genomic region the dominant chromatin state(s), without losing information on the remaining chromatin states. It furthermore suppresses genomic regions in which there is a lot of random variation (or confusion, or entropy) regarding chromatin states. And lastly, the information content IC(X) is strictly bounded between 0 and $\log_2$ (n) bits of information.

Figure 5:
FIG. 5 illustrates a relative frequency of occurrence of chromatin states in a human genome, using an example of a chromatin state model.

The inventors have recognized and appreciated that one disadvantage behind the notion of information content as described above is that the technique "expects" chromatin state calls to occur uniformly random across the genome, due to the uniform probability of occurrence calculated based on the number of possible chromatin states. It is certainly not the case that chromatin states occur uniformly; differences in probabilities of occurrence can span several orders of magnitude, as shown in FIG. 5. FIG. 5 shows a relative frequency of each chromatin state call across 127 epigenomes from the Roadmap Epigenomics Project. Colors correspond to the various chromatin states as defined in the Roadmap Epigenomics Project. The inventors have therefore recognized and appreciated that the formulae for entropy and information content in the example above may therefore falsely emphasize some chromatin states and falsely suppress other chromatin states.

Kullback-Leibler Divergence

The inventors have recognized and appreciated that one way to deal with a non-uniform distribution of chromatin state calls is to do an explicit comparison of an observed distribution to an expected distribution, in terms of the information content of the chromatin states. The inventors have recognized and appreciated that a Kullback-Leibler divergence, or relative entropy, may be used for this analysis.

Like with the information content measure described earlier, X is used to represent a random variable with n possible distinct values. For this random variable X, assume two distributions:

1. P: observed frequencies at a given single genomic position, i.e., based on a sampling from X at one genomic position across m epigenomes.
2. Q: expected frequencies based on the whole population, i.e., based on all possible samplings of X across all m epigenomes.

P and Q are defined to be described by probabilities p(i) and q(i), respectively, for each state i out of n states. Since P is based on a single 200 bp bin genomic position, its values p(i) are the unit normalized observed chromatin state frequencies at that single position. On the other hand, Q consists of the genome-wide frequencies q(i) of the n chromatin states, at all positions and across all epigenomes. (The inventors recognized that, using this approach, elements q(i) of Q are assumed to be the same across epigenomes. An alternative approach is described below.)

The Kullback-Leibler divergence of P versus Q, $D_{KL}(P\|Q)$, is then defined as:

$$D_{KL}(P\|Q) = -\sum_i p(i)\log_2(q(i)) + \sum_i p(i)\log_2(p(i)) \qquad (11)$$

$$= \sum_i p(i)\log_2(p(i)) - \sum_i p(i)\log_2(q(i)) \qquad (12)$$

$$= \sum_i p(i)\log_2\left(\frac{p(i)}{q(i)}\right). \qquad (13)$$

For any given chromatin state i, its contribution to $$D_{KL}(P\|Q) \text{ is } \log_2\left(\frac{p(i)}{q(i)}\right).$$

The Kullback-Leibler divergence gives the average number of additional bits needed to store the information in the observed distribution over that in the expected distribution. In other words, the higher the value of $D_{KL}(P\|Q)$, the more "surprising" the observed values, the more information is provided, and the higher the information content. The inventors have therefore recognized and appreciated that the Kullback-Leibler divergence is a good measure for emphasizing unexpected, and therefore potentially interesting, genomic sites.

Figure 6:
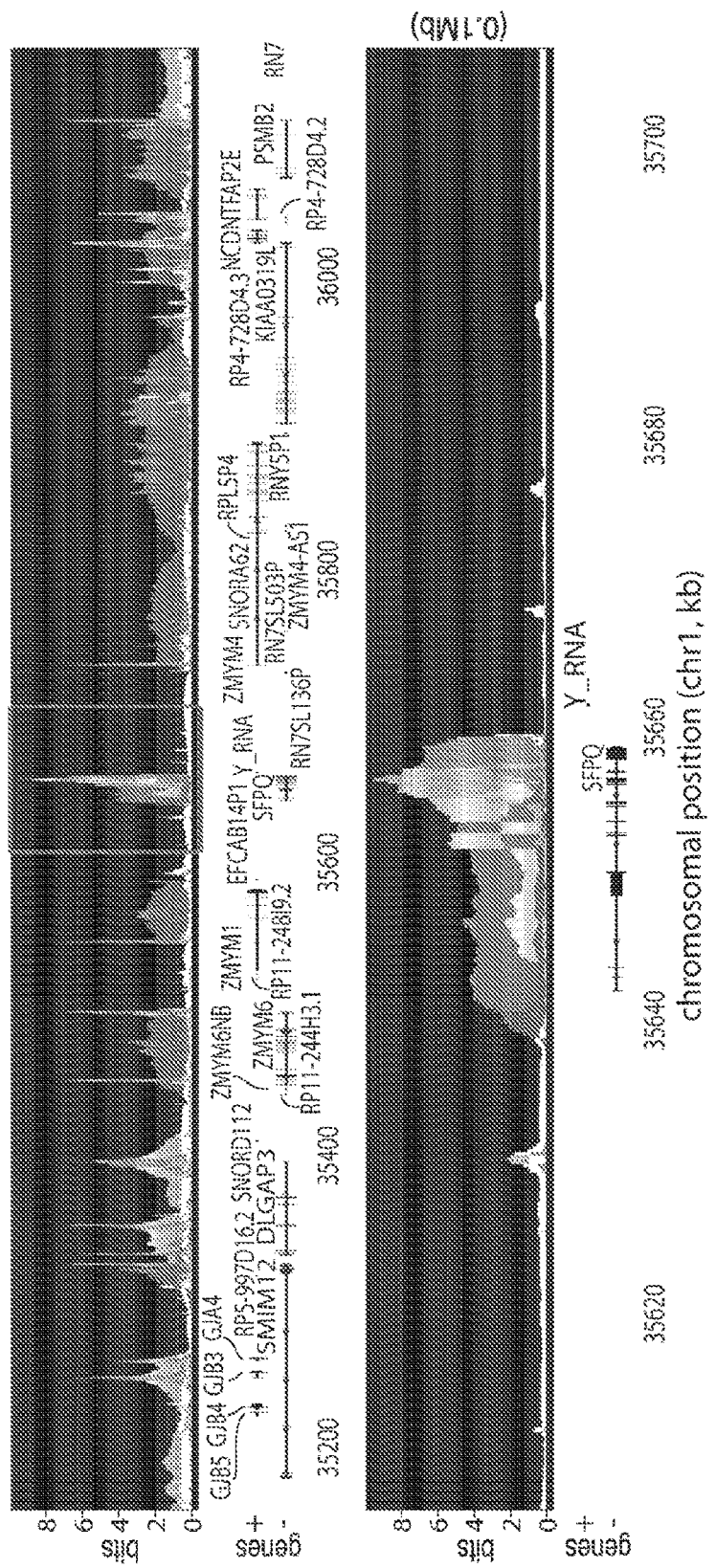
FIG. 6 is a visualization of epigenomic data produced using Kullbeck-Leibler information theoretic analysis in accordance with some techniques described herein.

Like for the Shannon information content, the Kullback-Leibler divergence can be visualized at each 200 bp region in the genome as a stack of all chromatin states occurring at that position, with the total height of the stack being $D_{KL}(P\|Q)$, and the chromatin states ordered by their individual relative occurrences. The height of a certain chromatin state i is set to be $p(i)D_{KL}(P\|Q)$. FIG. 6 illustrates an example of such a visualization. The visualization of FIG. 5 is formatted as described above in connection with FIG. 1. In the visualization, height indicates Kullback-Leibler divergence, or relative entropy, as compared to a uniform distribution of chromatin state calls. Heights of individual colors indicate relative occurrence counts of individual chromatin states.

The inventors have recognized and appreciated that an alternative way of visualizing the Kullback-Leibler divergence is to directly show the individual contributions of each state. For a given state i, this would be $$p(i)\log_2\left(\frac{p(i)}{q(i)}\right).$$

Figure 7:
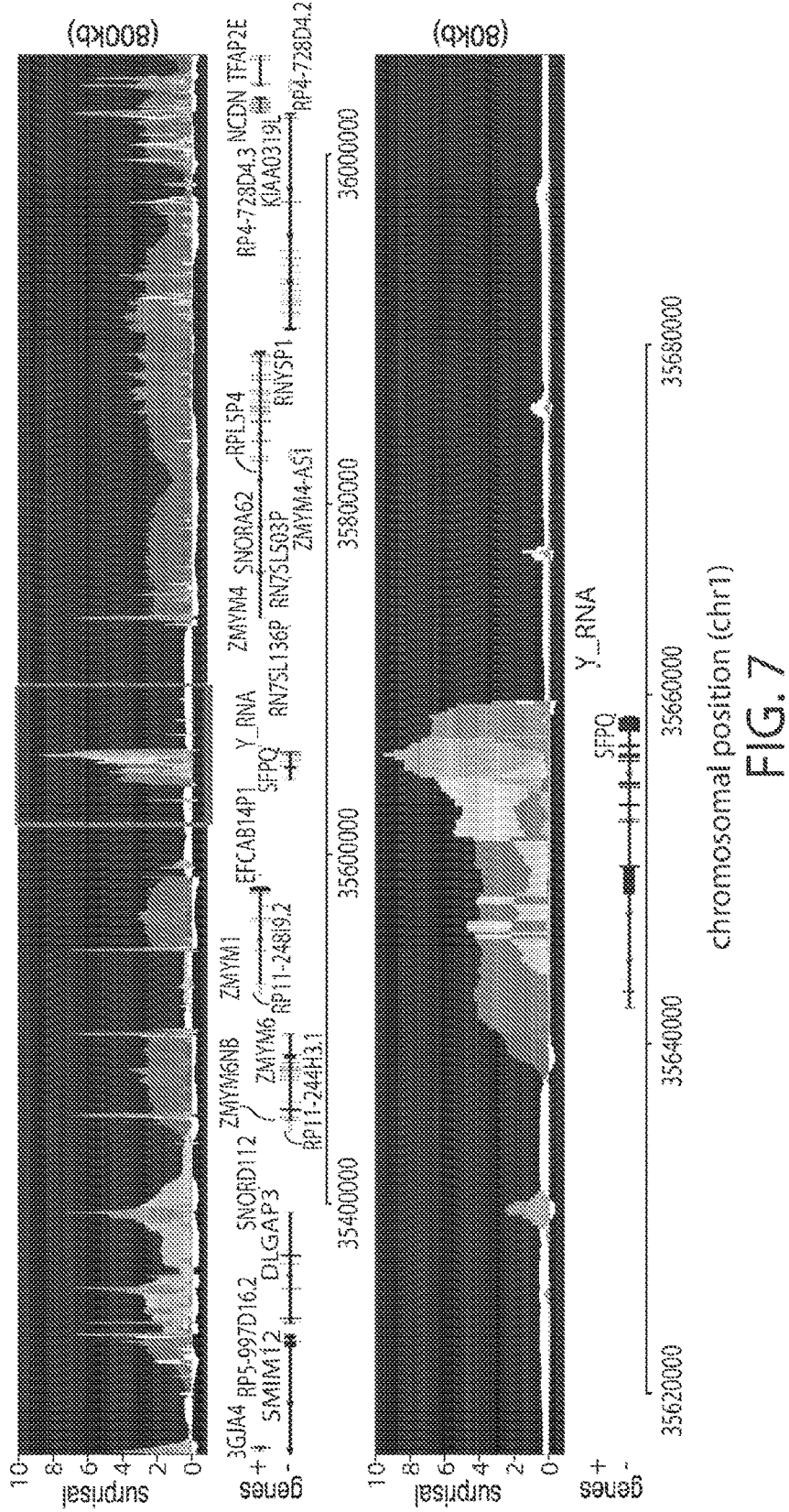
FIG. 7 is another visualization of epigenomic data produced using Kullbeck-Leibler information theoretic analysis in accordance with some techniques described herein.

This has the advantage that positive values for a state i represent an enrichment and negative values represent a depletion of that state relative to what is expected by chance. As such, the inventors have recognized and appreciated that such a visualization offers perhaps a more intuitive visualization of the "surprisal" at each genomic position, including information on the polarity of said surprisal. FIG. 7 illustrates an example of such a visualization. FIG. 7 is formatted as described above in connection with FIG. 1. FIG. 7 shows the contributions of individual chromatin states to the relative entropy, or Kullback-Leibler divergence, across 127 epigenomes. The sum at each position indicates Kullback-Leibler divergence, or relative entropy, as compared to a uniform distribution of chromatin state calls. Heights of individual colors indicate contributions of individual chromatin states to this Kullback-Leibler divergence.

Although the Kullback-Leibler method described here takes into account the genome-wide frequency of state calls, the inventors have recognized and appreciated that the method also assumes that these calls occur independently of each other at any given genomic site, and according to the same distribution across all m epigenomes. In other words, this Kullback-Leibler divergence assumes that all samplings across epigenomes occur from the same random variable X.

Figure 8:
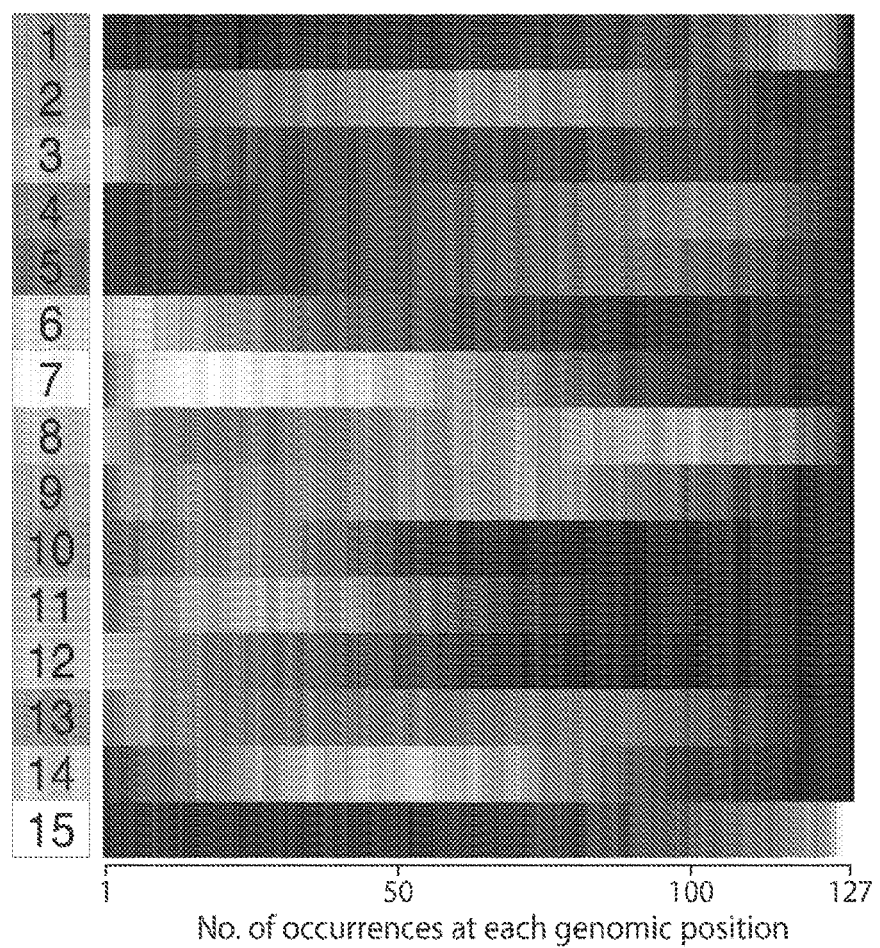
FIG. 8 illustrates a relative frequency of occurrence of chromatin states in a human genome across 127 cell types, using an example of a chromatin state model.

Such is certainly not the case, as some chromatin states (e.g., promoters) have the tendency to co-occur across many epigenomes at the same genomic site, whereas others (e.g., enhancers) are much more specific to single or small sets of epigenomes. This dependency phenomenon is illustrated in FIG. 8. FIG. 8 illustrates a relative number of occurrences of each chromatin state at any given genomic site. The plot shows relative distribution of the number of state call occurrences across 127 epigenomes at any given genomic location. Rows are scaled to sum to 1, after values were smoothed row-wise using a running mean filter of size 3. Colors correspond to the various chromatin states as defined in the Roadmap Epigenomics Project.

Relative Entropy with Dependency Statistics

The inventors have recognized and appreciated that the issue raised above regarding dependencies between chromatin states and epigenomes may be addressed in several ways. For example, every genomic position may be treated as a random vector of size m drawn from some unknown distribution. Each individual epigenome $\alpha$ can be described by a separate random variable $X_\alpha$, with an overall random variable $X=(X_1, X_2, \ldots, X_m)$. In practice, it may be very hard to estimate or model such a distribution, if only because of the large number of possible combinations of n states across m epigenomes.

Alternatively, the dependencies between pairs of states and epigenomes can be modeled by extending the Kullback-Leibler divergence calculation to explicitly model the dependencies. Modeling pairwise occurrences of chromatin states across epigenomes would effectively take into account the dependency structure that exists between them.

Dependencies Between Chromatin States

In this approach, first only the dependencies between chromatin states may be modeled. To do this, an n×n matrix Q* registering probabilities of two chromatin states i and j co-occurring at any given genomic location, or q(i, j) for short, is constructed. Q* is an empirical distribution based on averaging across all possible pairings of epigenomes.

Analogously, a matrix P* is defined as the unit normalized outer product of P, $P \otimes P$. This also results in an n×n matrix, but registering pairwise occurrence probabilities for one particular genomic region only, indicated by p(i, j). A pseudo-count may be added to P* at this point, but for simplicity may be omitted.

The following changes may be made to Equation 13 to take into account the joint probabilities:

$$D_{KL}(P^* \| Q^*) \sum_i \sum_j p(i, j) \log_2\left(\frac{p(i, j)}{q(i, j)}\right). \quad (14)$$

And in order to obtain relative surprisal levels for individual states, the following equation expression may be used:

$$\left\{ \sum_j p(i, j) \log_2\left(\frac{p(i, j)}{q(i, j)}\right) \mid \forall\, i \right\}.$$

Dependencies Between Chromatin States and Epigenomes

The next extension to the Kullback-Leibler divergence formula is to take into account dependencies between pairs of epigenomes as well. In order to do this, an n×n×m×m matrix Q registering probabilities of two chromatin states i and j co-occurring at any given genomic location in any two epigenomes $\alpha$ and $\beta$ may be constructed. This can be denoted by $\Pr[X_\alpha=i, X_\beta=j]$, or q(i, j, $\alpha$, $\beta$) for short. The matrix P then acts merely as a unit-normalized indicator function for registering which combinations of chromatin states and epigenomes occur at any given genomic position.

The Kullback-Leibler divergence formula may be extended to the following:

$$D_{KL}(P^{} \| Q^{}) \sum_i \sum_j \sum_\alpha \sum_\beta p(i, j, \alpha, \beta) \log_2\left(\frac{p(i, j, \alpha, \beta)}{q(i, j, \alpha, \beta)}\right). \quad (15)$$

Like before, in order to obtain relative surprisal levels for individual states, the following expression may be used:

$$\left\{ \sum_j \sum_\alpha \sum_\beta p(i, j, \alpha, \beta) \log_2\left(\frac{p(i, j, \alpha, \beta)}{q(i, j, \alpha, \beta)}\right) \mid \forall\, i \right\}.$$

Applications of Epilogos

A number of applications for the epilogos system are described below. In addition, some examples of ways in which the applications may be implemented or used are described.

Epigenome Browsing

The epilogos system, and the visualizations described above, provide an intuitive way of summarizing information across potentially large amounts of, for example, epigenomes. As such, it is well suited for exploratory data analysis through browsing.

Epilogos Across all Roadmap Epigenomics Epigenomes

Figure 9:
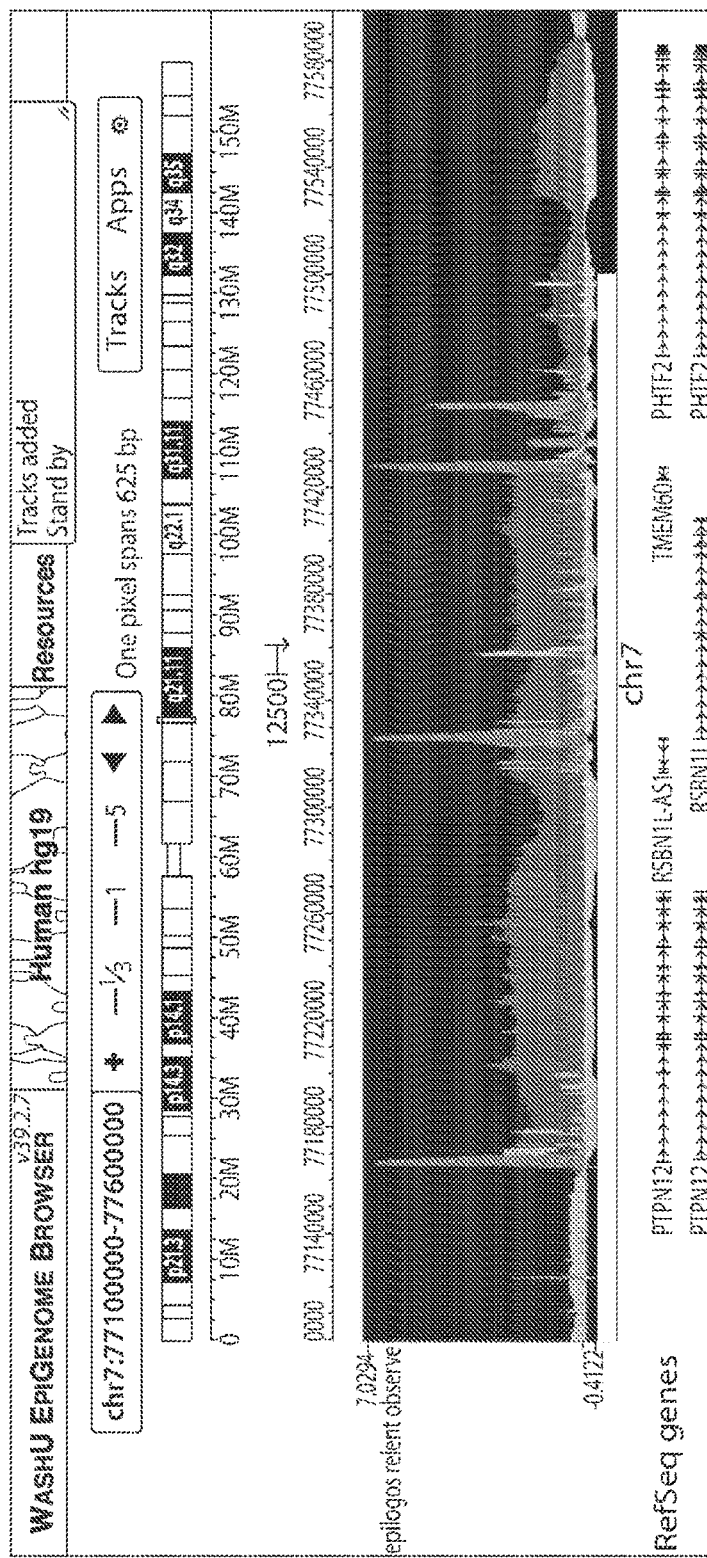
FIG. 9 is a screenshot of a visualization produced using a software application implementing some techniques described herein.

The epilogos system, and its visualizations based on all 127 Roadmap Epigenomics epigenomes, have been implemented in the epigenome browser available from the University of Washington (the "WashU Epigenome Browser"). An example of the visualizations in the browser is shown in FIG. 9. Specifically, FIG. 9 illustrates a visualization of a 500 kb region of chromosome 7 within the WashU Epigenome Browser.

Movies progressively showing parts of visualizations of a whole organism's genome may also be generated. For a human genome and 127 different cell types (and thus 127 different epigenomes), such a movie totals nearly 59 hours, using dynamic time sampling to emphasize differences in local information content.

Epilogos Across Custom Subsets of Roadmap Epigenomics Epigenomes

A web application may also be created to allow generation of epilogos visualizations based on arbitrary subsets of Roadmap Epigenomics epigenomes, selected by the user and provided as input.

Consensus Epigenomes

Figure 10:
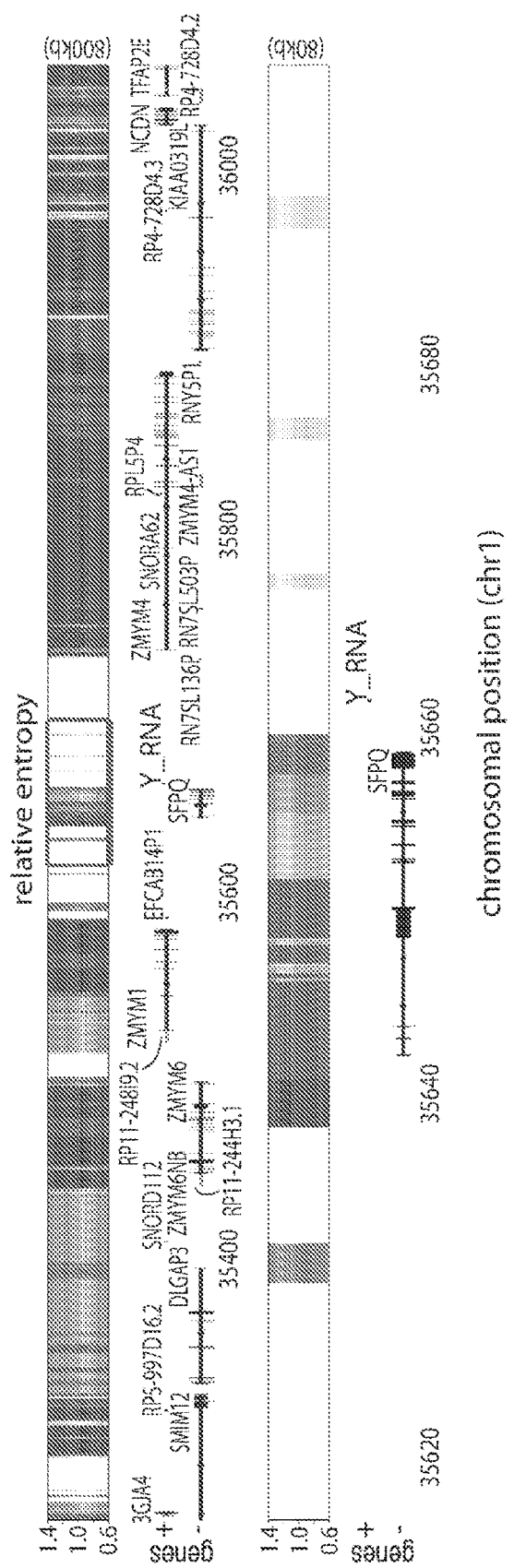
FIG. 10 is a visualization of a consensus epigenome sequence across 127 cell types for a set of genomic regions, produced in accordance with some techniques described herein.

The epilogos system allows for derivation of consensus chromatin states for each genomic region, which may be helpful in producing a consensus or reference epigenome. The consensus may reflect a sequence of chromatin states with the highest relative entropy or information content. FIG. 10 illustrates an example of such a sequence of consensus states, showing a same genomic region as was illustrated in FIG. 7.

As such, the consensus sequence is the strongest possible sequence of chromatin state calls representing the interrogated region. However, the inventors have recognized and appreciated that although the consensus sequence may be useful for purposes of summarizing data, the consensus sequence oftentimes does not represent an actual observed sequence of chromatin state calls. Because it does not fully capture the complexity of the epilogo, the inventors have recognized and appreciated that it may not be a fair representation of the underlying collection of chromatin state calls.

Similarly, nonsensus epigenomes and a nonsensus sequence may be derived by identifying chromatin state calls with the lowest relative entropy.

Comparative Epigenomics

Instead of performing an analysis using the full set of 127 Roadmap epigenomes, an analysis may be performed on any subset of them. Any suitable groups of cells may be used.

For example, an analysis may be performed for all stem cell(-like) samples. As another example, an analysis may be performed for all remaining (i.e., not stem cell or stem cell-like) epigenomes. An advantage of performing an analysis of a subset is that a comparison may then be performed of the results of analysis for the subsets. Specifically, statistical comparisons between the two sets of epilogos may be performed. For this comparison, regions with large differences between the two groups of cells may be identified.

Figure 11:
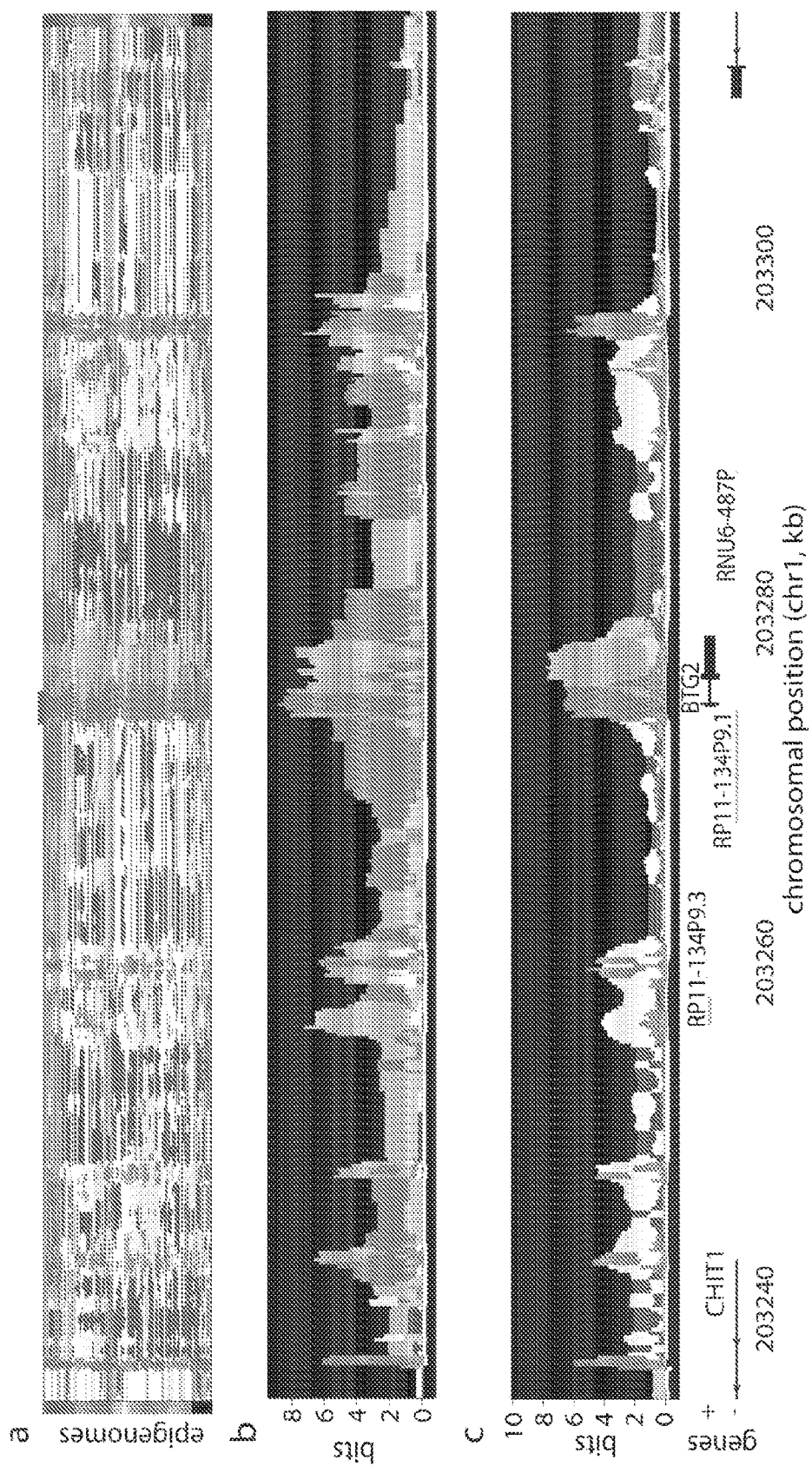
FIG. 11 includes a visualization of a comparison between epigenomic data produced in accordance with some techniques described herein, as well as a standard view for such epigenomic data.

For example, when considering the group of embryonic stem cells versus the rest of the 127 Roadmap Epigenomics epigenomes, one of the regions with the largest information difference to be a region in which the BTG2 gene resides, as shown in FIG. 11. FIG. 11 illustrates comparative epilogos visualizations for embryonic stem cells versus the other human epigenomes. FIG. 11 shows an 80 kb region of the human genome containing a sub-region in the center (indicated by a bar at the top) with a large information difference between two groups of epigenomes. The conventional way of showing chromatin states across all 127 epigenomes is labeled (a) in FIG. 11. Comparative epilogos for embryonic stem cells and the rest of the epigenomes are labeled (b) and (c), respectively.

Visualizations like the one of FIG. 11 may provide helpful biological information. BTG2 has been shown to inhibit cell-cycle progression. The graphics labeled (a) and (c) in FIG. 11 show that the gene is actively transcribed in most epigenomes, but is poised in embryonic stem cells as shown in the graph labeled (b).

Method

One way in which two groups of epigenomes may be compared is by comparing the chromatin state call occurrence counts between the two groups, for each 200 bp bin in the genome. To do so, a 2×n contingency table based on the number of occurrences of each of n chromatin states in the 2 groups of epigenomes may be constructed. The statistical test used for this may be Fisher's Exact Test. This gives a ρ-value for whether the two groups are significantly different.

Although this approach is very powerful, the inventors have recognized and appreciated that it does not take into account the information content carried in the different chromatin states. For this, a permutation-based approach may be used. For each comparison, separately for each chromatin state, an absolute difference in Kullback-Leibler divergence between the two groups may be calculated. These values are then summed to arrive at a general differential score for that comparison at a given region.

This is formulated as such for epigenome groups A and B.

$$KLdiff(X) = \sum_x \left| \left( p_x^A \log_2\left(\frac{p_x^A}{q(x)}\right) \right) - \left( p_x^B \log_2\left(\frac{p_x^B}{q(x)}\right) \right) \right| \quad (16)$$

Note that q(x) can either be the same for both groups, or be based on the two individual groups in case it can be replaced by $q_x^A$ and $q_x^B$. This score KLdiff (X) for a particular 200 bp position on the genome is then compared against a large number of scores derived from permuting the group labels and recalculating KLdiff (X*) for data with permuted labels (X*).

$$\binom{m}{k},$$

The total number of ways to select k elements out of a set of size m is defined by $$\frac{m!}{k!(m-k)!}.$$

For a typical comparison of one group of epigenomes of, e.g., size k=8, versus the rest of the epigenomes, m=127, this amounts to ≈1.34×10$^{12}$ different combinations.

These combinations will in principle contain many duplicates, especially as the number of unique states among the m epigenomes is limited. As an extreme case, if for a certain genomic position all epigenomes are in state i, although there are technically $$\binom{m}{k}$$

combinations, in an order-invariant manner there is only 1.

The inventors appreciate that this may be an extreme example, as in reality there are usually multiple states involved. Such scenarios may be modeled using so called "multisets", defined as sets of size k drawn from n unique elements (or in this cases: chromatin states) with replacement. That is, the number of occurrences of a particular element in a multiset can be larger than 1. The number of multisets of size k from a set of n possible unique elements (chromatin states), is denoted as $$\left(\!\binom{n}{k}\!\right)$$

and given by:

$$\frac{(n+k-1)!}{k!(n-1)!}.$$

The problem here, is that the number of replacement draws of a particular element i is not limited to the actual number of occurrences of that element in the m total epigenomes. In order to obtain the number of possible order-invariant permutations while retaining information of the total number of occurrences of each of the n different elements, the Inclusion-Exclusion principle may be used, as follows:

$$\left| \bigcup_{1 \le i \le n} A_i \right| = \sum_{1 \le i_1 \le n} |A_{i_1}| - \sum_{1 \le i_1 \le i_2 \le n} |A_{i_1} \cap A_{i_2}| + \sum_{1 \le i_1 \le i_2 \le i_3 \le n} |A_{i_1} \cap A_{i_2} \cap A_{i_3}| - \ldots + (-1)^{n+1} \left| \bigcap_{i=1}^n A_i \right|.$$

Apart from being able to serve as an empirical ρ-value, the fraction of unique permutations that yield a KLdiff(X*) score below the KLdiff (X) score of the original/observed data is an indication of the "specificity" of the particular comparison. In case the number of possible permutation is (much) larger than 100,000, a random sampling of possible scenarios may be performed to calculate the specificity score (and empirical ρ-value).

Pattern Discovery

A promising application of the epilogos system may be the ability to discover patterns in chromatin states. This may be used for finding patterns within a single genomic region across many cells types and epigenomes. This may also be used to identify patterns in chromatin state call occurrences across multiple genomic regions. An example of the latter is provided below.

Rapid Multi-Site Summarization

To do so, the epilogos system is first used to quickly summarize chromatin state information across many genomic regions. As an example, the 1,000 most highly expressed genes in human H1 embryonic stem cells, based on data from the Roadmap Epigenomics project, may be selected. Next, chromatin states for 16 kb regions centered around the transcription start sites (TSSs) of these genes are selected, to make sure to orient chromatin state call sequences as per the strand-direction of the genes.

Figure 12:
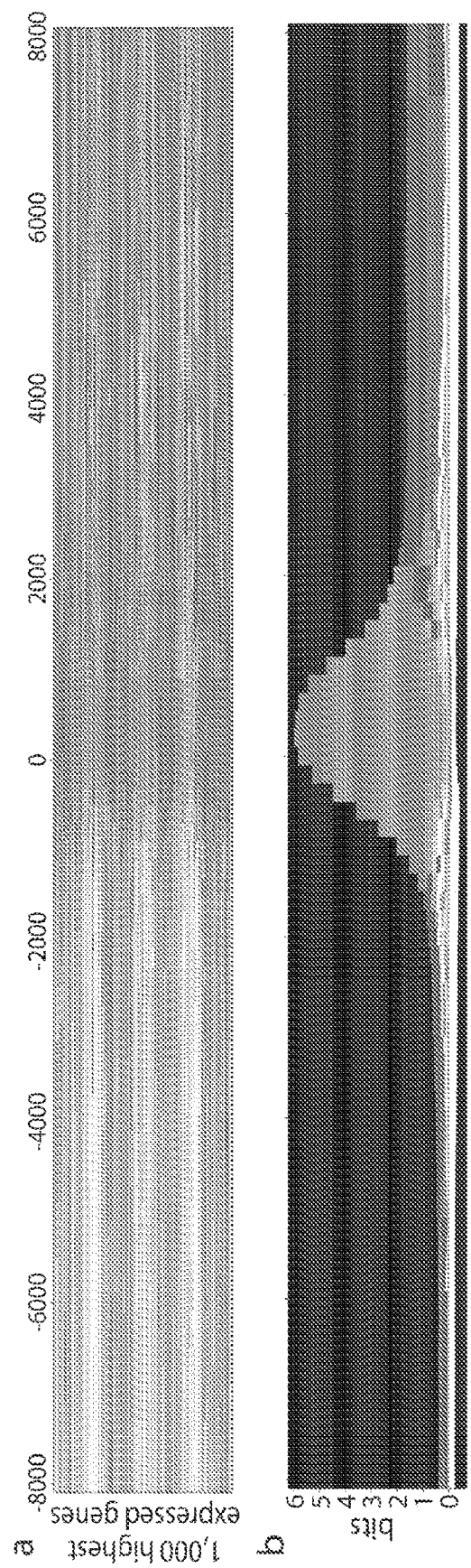
FIG. 12 is a visualization of epigenomic data produced in accordance with some techniques described herein.

Relying on the alignment around known TSSs, an epilogos visualization may then be generated across the 1,000 selected regions using the information theory techniques described above. The result is shown in FIG. 12. FIG. 12 illustrates a rapid summarization of 1,000 transcription start sites of active genes, by illustrating chromatin state calls for 16 kb regions around transcription start sites of 1,000 genes found to be highly expressed in human H1 embryonic stem cells. The graph labeled (a) shows a traditional view, while the graph labeled (b) shows a visualization produced using the epilogos system.

The data shown in FIG. 12 reveal a general pattern that is well-associated with knowledge regarding TSSs of actively transcribed genes, while still taking into account the information content of each chromatin state at each position.

Pattern Discovery in Non-Aligned Sequences

In foregoing examples, alignment of sequences was performed with reference to a certain known landmark, such as a set genomic location or around transcription start sites. The inventors have recognized and appreciated that for many practical applications of pattern identification, such landmarks will not be available. The inventors have additionally recognized and appreciated, however, that the approach of finding epigenomic patterns in unaligned sequences is analogous to de novo motif finding and that these techniques may be used in pattern identification.

Expectation Maximization and Gibbs sampling are proven concepts used in amino-acid and DNA sequence modeling. When used in the epilogos system, these techniques may allow for the pre-selection of a number of regions of interest and the discovery of common epigenomic patterns in these regions. The power of these methods stems in part from the fact that the pre-selected regions do not have to be aligned.

Figure 13:
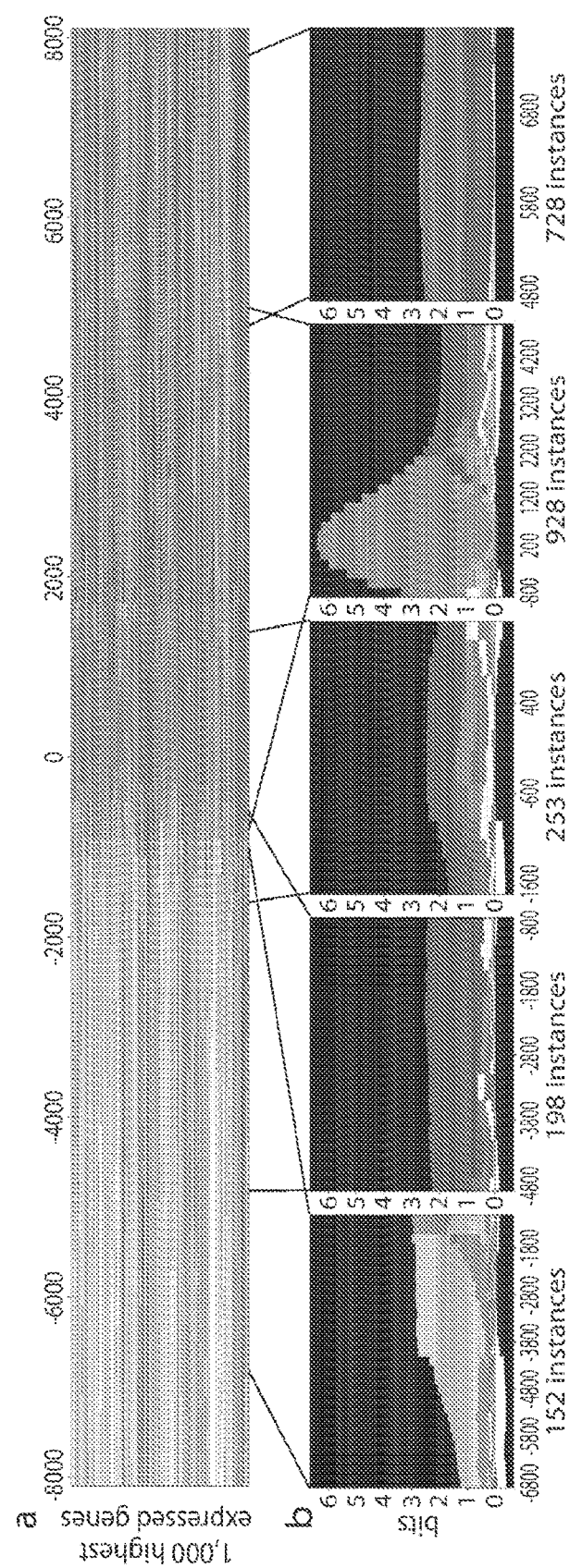
FIG. 13 is a visualization of information regarding patterns detected in epigenomic data using some techniques described herein.

A well known piece of software to perform Expectation Maximization-based pattern discovery in biological sequences is known as MEME. The MEME software may be adapted to work with alphabets based on chromatin states, instead of nucleotides or amino acids, and have adjusted background frequencies and priors accordingly. With such adaptations, the MEME software may be used to identify patterns in epigenomic data. Using the adapted software, five common epigenomic patterns have been identified and subsequently visualized using the epilogos system, and related to the position where the patterns were found. FIG. 13 shows a result of this analysis. FIG. 13 illustrates a result of pattern discovery using Expectation Maximization (MEME) in TSSs of 1,000 active genes. In FIG. 13, chromatin state calls for 16 kb regions around transcription start sites of 1,000 genes found to be highly expressed in human H1 embryonic stem cells are shown. The graph labeled (a) shows a traditional view and the graph labeled (b) shows five epilogos patterns discovered using Expectation Maximization. Note that the positioning illustrated in FIG. 13 is approximate, as even though aligned epigenomic sequences were used, there may still be slight positional variation as well as multiple occurrences.

The patterns discovered in the TSS regions of the 1,000 active genes correspond with what is known about these regions. Namely, high levels of the H3K4me3 histone tail modification results in the various TSS chromatin states, and H3K36me3 enrichments show up as transcribed regions. This is all in accordance with known biology.

Figure 14:
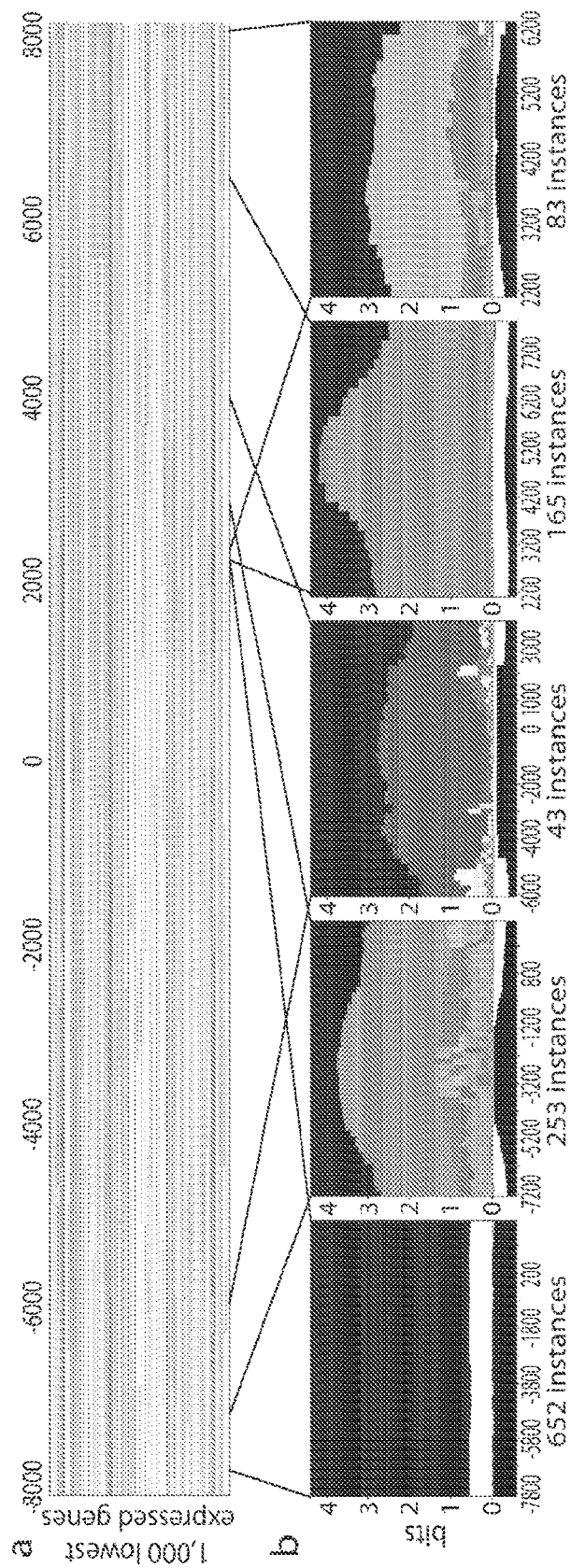
FIG. 14 is a visualization of information regarding patterns detected in epigenomic data using some techniques described herein.

A follow-up question could be what the 1,000 lowest expressed genes look like, in terms of chromatin state calls around their TSSs. The result of performing Expectation Maximization-based pattern discovery on these regions is shown in FIG. 14. FIG. 14 shows a result of pattern discovery using Expectation Maximization in TSSs of 1,000 inactive genes. The visualization of FIG. 14 is the same as described above for FIG. 13, except FIG. 14 uses the 1,000 lowest expressed genes.

Although the most prevalent pattern of FIG. 14 (left, 652 instances) shows an enrichment for the "Quiescent" chromatin state, several less prevalent patterns involving repressive chromatin states and marks (i.e., H3K9me3 and H3K27me3) are shown. Some weak transcription-like patterns in a subset of regions are also shown.

With these techniques, the epilogos system may allow one to perform meaningful pattern discovery and modeling, in large numbers of epigenomes and regions.

Examples of Implementation Using One or More Computing Devices

Techniques operating according to the principles described herein may be implemented in any suitable manner. Included in the discussion above are a series of flow charts showing the steps and acts of various processes that analyze genomic regions such as by determining an information content of the regions based on chromatin state data for the regions. The processing and decision blocks of the flow charts above represent steps and acts that may be included in algorithms that carry out these various processes. Algorithms derived from these processes may be implemented as software integrated with and directing the operation of one or more single- or multi-purpose processors, may be implemented as functionally-equivalent circuits such as a Digital Signal Processing (DSP) circuit or an Application-Specific Integrated Circuit (ASIC), or may be implemented in any other suitable manner. It should be appreciated that the flow charts included herein do not depict the syntax or operation of any particular circuit or of any particular programming language or type of programming language. Rather, the flow charts illustrate the functional information one skilled in the art may use to fabricate circuits or to implement computer software algorithms to perform the processing of a particular apparatus carrying out the types of techniques described herein. It should also be appreciated that, unless otherwise indicated herein, the particular sequence of steps and/or acts described in each flow chart is merely illustrative of the algorithms that may be implemented and can be varied in implementations and embodiments of the principles described herein.

Accordingly, in some embodiments, the techniques described herein may be embodied in computer-executable instructions implemented as software, including as application software, system software, firmware, middleware, embedded code, or any other suitable type of computer code. Such computer-executable instructions may be written using any of a number of suitable programming languages and/or programming or scripting tools, and also may be compiled as executable machine language code or intermediate code that may be executed on a framework or virtual machine.

When techniques described herein are embodied as computer-executable instructions, these computer-executable instructions may be implemented in any suitable manner, including as a number of functional facilities, each providing one or more operations to complete execution of algorithms operating according to these techniques. A "functional facility," however instantiated, is a structural component of a computer system that, when integrated with and executed by one or more computers, causes the one or more computers to perform a specific operational role. A functional facility may be a portion of or an entire software element. For example, a functional facility may be implemented as a function of a process, or as a discrete process, or as any other suitable unit of processing. If techniques described herein are implemented as multiple functional facilities, each functional facility may be implemented in its own way; all need not be implemented the same way. Additionally, these functional facilities may be executed in parallel and/or serially, as appropriate, and may pass information between one another using a shared memory on the computer(s) on which they are executing, using a message passing protocol, or in any other suitable way.

Generally, functional facilities include routines, programs, objects, components, data structures, etc. that perform particular tasks or implement particular abstract data types. Typically, the functionality of the functional facilities may be combined or distributed as desired in the systems in which they operate. In some implementations, one or more functional facilities carrying out techniques herein may together form a complete software package. These functional facilities may, in alternative embodiments, be adapted to interact with other, unrelated functional facilities and/or processes, to implement a software program application.

Some exemplary functional facilities have been described herein for carrying out one or more tasks. It should be appreciated, though, that the functional facilities and division of tasks described is merely illustrative of the type of functional facilities that may implement the exemplary techniques described herein, and that embodiments are not limited to being implemented in any specific number, division, or type of functional facilities. In some implementations, all functionality may be implemented in a single functional facility. It should also be appreciated that, in some implementations, some of the functional facilities described herein may be implemented together with or separately from others (i.e., as a single unit or separate units), or some of these functional facilities may not be implemented.

Computer-executable instructions implementing the techniques described herein (when implemented as one or more functional facilities or in any other manner) may, in some embodiments, be encoded on one or more computer-readable media to provide functionality to the media. Computer-readable media include magnetic media such as a hard disk drive, optical media such as a Compact Disk (CD) or a Digital Versatile Disk (DVD), a persistent or non-persistent solid-state memory (e.g., Flash memory, Magnetic RAM, etc.), or any other suitable storage media. Such a computer-readable medium may be implemented in any suitable manner, including as computer-readable storage media 1506 of FIG. 15 described below (i.e., as a portion of a computing device 1500) or as a stand-alone, separate storage medium. As used herein, "computer-readable media" (also called "computer-readable storage media") refers to tangible storage media. Tangible storage media are non-transitory and have at least one physical, structural component. In a "computer-readable medium," as used herein, at least one physical, structural component has at least one physical property that may be altered in some way during a process of creating the medium with embedded information, a process of recording information thereon, or any other process of encoding the medium with information. For example, a magnetization state of a portion of a physical structure of a computer-readable medium may be altered during a recording process.

In some, but not all, implementations in which the techniques may be embodied as computer-executable instructions, these instructions may be executed on one or more suitable computing device(s) operating in any suitable computer system, or one or more computing devices (or one or more processors of one or more computing devices) may be programmed to execute the computer-executable instructions. A computing device or processor may be programmed to execute instructions when the instructions are stored in a manner accessible to the computing device or processor, such as in a data store (e.g., an on-chip cache or instruction register, a computer-readable storage medium accessible via a bus, etc.). Functional facilities comprising these computer-executable instructions may be integrated with and direct the operation of a single multi-purpose programmable digital computing device, a coordinated system of two or more multi-purpose computing device sharing processing power and jointly carrying out the techniques described herein, a single computing device or coordinated system of computing device (co-located or geographically distributed) dedicated to executing the techniques described herein, one or more Field-Programmable Gate Arrays (FPGAs) for carrying out the techniques described herein, or any other suitable system.

Figure 15:
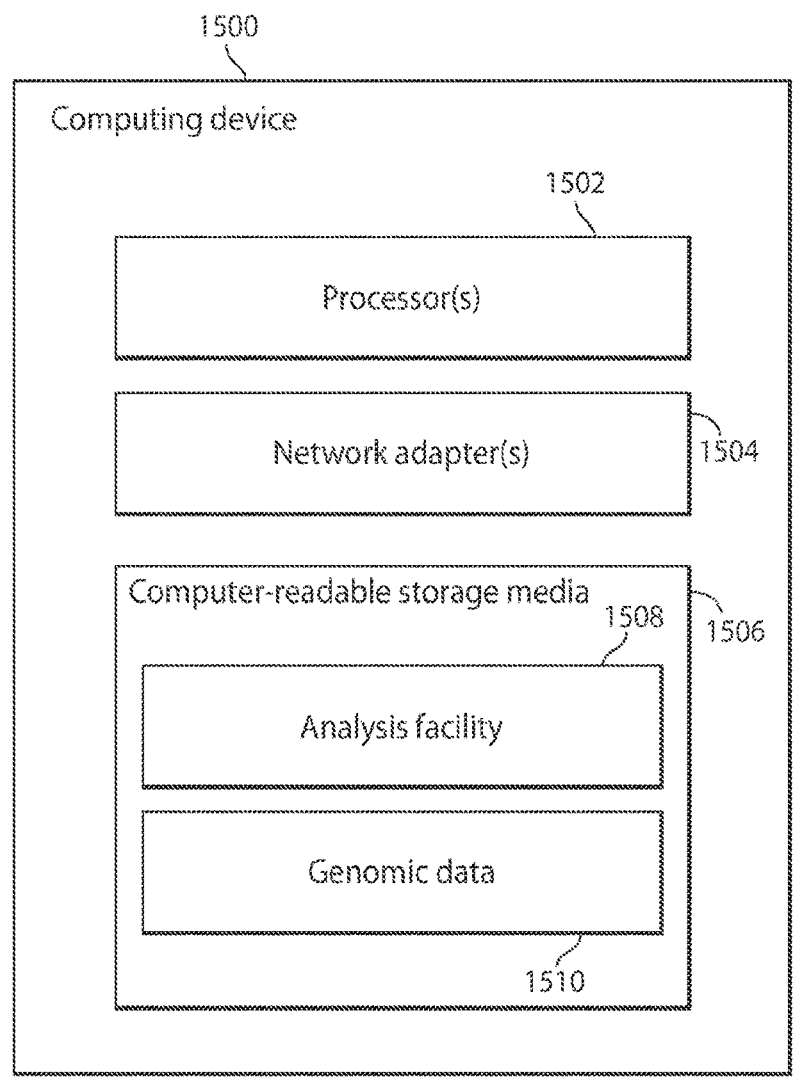
FIG. 15 is a block diagram of an example of a computing device with which some embodiments may operate.

FIG. 15 illustrates one exemplary implementation of a computing device in the form of a computing device 1500 that may be used in a system implementing techniques described herein, although others are possible. It should be appreciated that FIG. 15 is intended neither to be a depiction of necessary components for a computing device to operate in accordance with the principles described herein, nor a comprehensive depiction.

Computing device 1500 may comprise at least one processor 1502, a network adapter 1504, and computer-readable storage media 1506. Computing device 1500 may be, for example, a desktop or laptop personal computer, a personal digital assistant (PDA), a smart mobile phone, a server, or any other suitable computing device. Network adapter 1504 may be any suitable hardware and/or software to enable the computing device 1500 to communicate wired and/or wirelessly with any other suitable computing device over any suitable computing network. The computing network may include wireless access points, switches, routers, gateways, and/or other networking equipment as well as any suitable wired and/or wireless communication medium or media for exchanging data between two or more computers, including the Internet. Computer-readable media 1506 may be adapted to store data to be processed and/or instructions to be executed by processor 1502. Processor 1502 enables processing of data and execution of instructions. The data and instructions may be stored on the computer-readable storage media 1506 and may, for example, enable communication between components of the computing device 1500.

The data and instructions stored on computer-readable storage media 1506 may comprise computer-executable instructions implementing techniques which operate according to the principles described herein. In the example of FIG. 15, computer-readable storage media 1506 stores computer-executable instructions implementing various facilities and storing various information as described above. Computer-readable storage media 1506 may store an analysis facility 1508 that performs analysis techniques as described above, which may include visualization techniques discussed above to create and output (e.g., output for display or display) a visualization. For example, in some cases the analysis facility 1508 may form a portion of a genome browser, as discussed above. In addition, the media 1506 may store genomic data 1510 that includes information on chromatin states for genomic regions and/or information on which chromatin states for genomic regions may be identified.

While not illustrated in FIG. 15, a computing device may additionally have one or more components and peripherals, including input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computing device may receive input information through speech recognition or in other audible format.

Embodiments have been described where the techniques are implemented in circuitry and/or computer-executable instructions. It should be appreciated that some embodiments may be in the form of a method, of which at least one example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

Various aspects of the embodiments described above may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Also, the phraseology and terminology used herein is for the purpose of description and should not be regarded as limiting. The use of "including," "comprising," "having," "containing," "involving," and variations thereof herein, is meant to encompass the items listed thereafter and equivalents thereof as well as additional items.

The word "exemplary" is used herein to mean serving as an example, instance, or illustration. Any embodiment, implementation, process, feature, etc. described herein as exemplary should therefore be understood to be an illustrative example and should not be understood to be a preferred or advantageous example unless otherwise indicated.

Having thus described several aspects of at least one embodiment, it is to be appreciated that various alterations, modifications, and improvements will readily occur to those skilled in the art. Such alterations, modifications, and improvements are intended to be part of this disclosure, and are intended to be within the spirit and scope of the principles described herein. Accordingly, the foregoing description and drawings are by way of example only.

What is claimed is:

1. A method comprising:
   operating at least one processor to carry out acts of:
      for each genomic region of at least one genomic region, of a plurality of genomic regions of a genome for a first type of organism, determining an information content of the genomic region for the first type of organism, wherein determining the information content of the genomic region for the first type of organism comprises:
         receiving digital data identifying, for a plurality of cells of the first type of organism having the genome, one or more chromatin states associated with the genomic region in the plurality of cells, each of the chromatin states associated with the genomic region being a chromatin state from a set of two or more chromatin states, wherein each chromatin state of the set is associated with a different set of one or more chromatin characteristics; and
         determining the information content of the genomic region for the first type of organism indicating an amount of information provided by the one or more chromatin states associated with the genomic region in the plurality of cells, wherein determining the information content of the genomic region for the first type of organism comprises comparing an observed occurrence of a chromatin state in the genomic region in the plurality of cells to an expected occurrence of the chromatin state in the plurality of cells;
      for each genomic region of at least one second genomic region, of a second plurality of genomic regions of a second genome for a second type of organism, determining an information content of the genomic region for the second type of organism;
      comparing the information content for each genomic region of the at least one genomic region for the first type of organism and the at least one second genomic region for the second type of organism; and
      storing the information content for each genomic region of the at least one genomic region for the first type of organism in at least one data store.

2. The method of claim 1, wherein:
   the digital data identifies chromatin states for cells of the first type of organism and cells of the second type of organism for each genomic region of the at least one genomic region for the first type of organism and the at least one second genomic region for the second type of organism; and
   determining the information content of the genomic region for the first type of organism indicating the amount of information provided by the one or more chromatin states comprises determining an information content for each chromatin state associated with the genomic region in the cells of the first type of organism.

3. The method of claim 2, wherein determining the information content of the genomic region for the first type of organism comprises determining the information content of the genomic region from the information content for each chromatin state associated with the genomic region in the cells of the first type of organism.

4. The method of claim 1, wherein determining the information content of the genomic region for the first type of organism indicating the amount of information provided by the one or more chromatin states comprises evaluating a probability of occurrence of the one or more chromatin states at the genomic region.

5. The method of claim 1, wherein:
receiving the digital data identifying the one or more chromatin states associated with the genomic region in the plurality of cells comprises receiving digital data identifying chromatin states associated with the genomic region in cells of the first type of organism and cells of the second type of organism, the cells of the first type of organism and the cells of the second type of organism comprising the plurality of cells; and
determining the information content of the genomic region for the first type of organism indicating the amount of information provided by the one or more chromatin states comprises comparing an observed occurrence of a chromatin state in the genomic region in the cells of the first type of organism to an expected occurrence of the chromatin state in the cells on the first type of organism.

6. The method of claim 5, wherein:
the method further comprises:
receiving digital data identifying chromatin states associated with one or more other genomic regions in the cells of the first type of organism and the cells of the second type of organism; and
determining the expected occurrence of the chromatin state in the genomic region based on occurrence of the chromatin state in the genomic region and the one or more other genomic regions in the cells of the first type of organism.

7. The method of claim 5, wherein:
the method further comprises:
receiving digital data identifying chromatin states associated with one or more other genomic regions in the cells of the first type of organism and the cells of the second type of organism; and
determining the expected occurrence of the chromatin state in the genomic region based on a number of times, for each genomic region of the genomic region and the one or more other genomic regions, that the chromatin state appears at the genomic region in cells of the first type of organism.

8. The method of claim 5, wherein:
the method further comprises:
receiving digital data identifying chromatin states associated with one or more other genomic regions in the cells of the first type of organism and the cells of the second type of organism;
analyzing the digital data identifying the chromatin states associated with the genomic region and the one or more other genomic regions in the cells of the first type of organism to identify one or more relationships in occurrence of chromatin states in the genomic region and the one or more other genomic regions in the cells of the first type of organism; and
determining the expected occurrence of the chromatin state in the genomic region based at least in part on the one or more relationships in occurrence of chromatin states.

9. The method of claim 5, wherein the cells of the first type of organism and the cells of the second type of organism include cells of a single cell type.

10. The method of claim 1, further comprising operating the at least one processor to carry out acts of:
determining one or more genomic regions of the at least one genomic region for the first type of organism for which an information content of the genomic region satisfies at least one criteria; and
outputting an identification of the one or more genomic regions for which an information content satisfies the at least one criteria.

11. The method of claim 10, wherein determining the one or more genomic regions of the at least one genomic region for the first type of organism for which the information content for the genomic region satisfies the at least one criteria comprises determining genomic regions having an information content above a threshold.

12. The method of claim 1, wherein:
determining the information content for each genomic region of the at least one genomic region for the first type of organism comprises, for each genomic region, determining a first information content for each chromatin state associated with the genomic region;
determining the information content for each genomic region of the at least one second genomic region for the second type of organism comprises, for each genomic region, determining a second information content for each chromatin state associated with the second genomic region; and
comparing the information content for each genomic region of the at least one genomic region for the first type of organism and the at least one second genomic region for the second type of organism comprises, for each genomic region:
determining a difference in information contents for one or more chromatin states in the genomic region between the first type of organism and the second type of organism, and
summing differences in information contents for the chromatin states for the genomic region.

13. The method of claim 1, wherein:
the first type of organism is a male organism of a species; and
the second type of organism is a female organism of the species.

14. The method of claim 1, wherein:
the first type of organism is a first species; and
the second type of organism is a second species.

15. The method of claim 1, wherein:
the first type of organism is an organism of a control group for a species; and
the second type of organism is an organism of the species having at least one characteristic that organisms of the at least one control group for the species do not have.

16. At least one computer-readable storage medium having encoded thereon executable instructions that, when executed by at least one processor, cause the at least one processor to carry out a method comprising:
for each genomic region of at least one genomic region, of a plurality of genomic regions of a genome for a first type of organism, determining an information content of the genomic region for the first type of organism, wherein determining the information content of the genomic region for the first type of organism comprises:
receiving digital data identifying, for a plurality of cells of the first type of organism having the genome, a chromatin state associated with the genomic region in the plurality of cells, the chromatin state associated with the genomic region being a chromatin state from a set of two or more chromatin states, wherein each chromatin state of the set is associated with a different set of one or more chromatin characteristics; and
determining the information content of the genomic region for the first type of organism indicating an amount of information provided by the chromatin state associated with the genomic region in the plurality of cells, wherein determining the information content of the genomic region for the first type of organism comprises comparing an observed occurrence of a chromatin state in the genomic region in the plurality of cells to an expected occurrence of the chromatin state in the plurality of cells;
for each genomic region of at least one second genomic region, of a second plurality of genomic regions of a second genome for a second type of organism, determining an information content of the genomic region;
comparing the information content for each genomic region of the at least one genomic region for the first type of organism and the at least one second genomic region for the second type of organism; and
storing the information content for each genomic region of the at least one genomic region for the first type of organism in at least one data store.

17. An apparatus comprising:
at least one processor; and
at least one storage medium having encoded thereon executable instructions that, when executed by the at least one processor, cause the at least one processor to carry out a method comprising:
for each genomic region of at least one genomic region, of a plurality of genomic regions of a genome for a first type of organism, determining an information content of the genomic region for the first type of organism, wherein determining the information content of the genomic region for the first type of organism comprises:
receiving digital data identifying, for a plurality of cells of the first type of organism having the genome, a chromatin state associated with the genomic region in the plurality of cells, the chromatin state associated with the genomic region being a chromatin state from a set of two or more chromatin states, wherein each chromatin state of the set is associated with a different set of one or more chromatin characteristics; and
determining the information content of the genomic region for the first type of organism indicating an amount of information provided by the chromatin state associated with the genomic region in the plurality of cells, wherein determining the information content of the genomic region for the first type of organism comprises comparing an observed occurrence of a chromatin state in the genomic region in the plurality of cells to an expected occurrence of the chromatin state in the plurality of cells;
for each genomic region of at least one second genomic region, of a second plurality of genomic regions of a second genome for a second type of organism, determining an information content of the genomic region;
comparing the information content for each genomic region of the at least one genomic region for the first type of organism and the at least one second genomic region for the second type of organism; and
storing the information content for each genomic region of the at least one genomic region for the first type of organism in at least one data store.

* * * * *

UNITED STATES PATENT AND TRADEMARK OFFICE
CERTIFICATE OF CORRECTION

| | |
|---|---|
| PATENT NO. | : 11,195,596 B2 |
| APPLICATION NO. | : 15/547240 |
| DATED | : December 7, 2021 |
| INVENTOR(S) | : Wouter Meuleman |

It is certified that error appears in the above-identified patent and that said Letters Patent is hereby corrected as shown below:

In the Claims

At Column 41, Claim 5, Line 32, "the chromatin state in the cells on the first" should read --the chromatin state in the cells of the first--

Signed and Sealed this
Twenty-sixth Day of July, 2022

Katherine Kelly Vidal
*Director of the United States Patent and Trademark Office*